(12) United States Patent
Grabherr et al.

(10) Patent No.: US 9,297,014 B2
(45) Date of Patent: Mar. 29, 2016

(54) HOST-VECTOR SYSTEM ANTIBIOTIC-FREE COLE1 PLASMID PROPAGATION

(75) Inventors: Reingard Grabherr, Pressbaum (AT); Irene Pfaffenzeller, Vienna (AT)

(73) Assignee: BOEHRINGER INGELHEIM RCV GMBH & CO KG, Vienna (AT)

( * ) Notice: Subject to any disclaimer, the term of this patent is extended or adjusted under 35 U.S.C. 154(b) by 843 days.

(21) Appl. No.: 12/259,662

(22) Filed: Oct. 28, 2008

(65) Prior Publication Data

US 2009/0263861 A1   Oct. 22, 2009

Related U.S. Application Data

(63) Continuation of application No. 11/226,795, filed on Sep. 14, 2005, now abandoned.

(30) Foreign Application Priority Data

Sep. 17, 2004 (EP) .................................... 04022201

(51) Int. Cl.
   *C12N 1/20* (2006.01)
   *C12P 19/34* (2006.01)
   *C12N 15/70* (2006.01)

(52) U.S. Cl.
   CPC ...................................... *C12N 15/70* (2013.01)

(58) Field of Classification Search
   None
   See application file for complete search history.

(56) References Cited

U.S. PATENT DOCUMENTS

| 7,611,883 | B2 | 11/2009 | Cranenburgh |
| 2007/0110721 | A1 | 5/2007 | Cranenburgh |
| 2009/0227658 | A1* | 9/2009 | Huang et al. ................. 514/44 R |

FOREIGN PATENT DOCUMENTS

| CA | 2546775 A1 | 6/2005 |
| WO | 94/02607 A1 | 2/1994 |
| WO | 03/000881 A2 | 1/2003 |
| WO | 2005/052167 A2 | 6/2005 |
| WO | 2005/052167 A3 | 7/2005 |

OTHER PUBLICATIONS

Balbas, Paulina., et al; Understanding the Art of Producing Protein and Nonprotein Molecules in *Escherichia coli;* Molecular Biotechnology (2001) vol. 19, No. 3 pp. 251-267.
Casali, Nicola ; *Eschirichia coli* Host Strains; Methods Molecular Biology (2003) vol. 253 pp. 27-48.
Gregorian, Razmic S., et al; Determinants of RNA Hairpin Loop-Loop Complex Stability; Journal of Molecular Biology (1995) vol. 248 pp. 968-984.
Guzman, Luz-Maria., et al; Tight Regulation, Modulation, and High-Level expression by Vectors Containing the Arabinose $P_{BAD}$ Promoter; Journal of Bacteriology (1995) vol. 177, No. 14 pp. 4121-4130.
Haegg, Peter., et al; A Host/Plasmid System that is not Dependent on Antibiotics and Antibiotic Genes for Stable Plasmid Maintenance in *Eschericia coli*; Journal of Biotechnology (2004) vol. 111 pp. 17-30.
Haidinger, W., et al; Online Monitoring of *Escherichia coli* Ghost Production; Applied and Environmental Microbiology (2003) vol. 69, No. 1 pp. 468-474.
Helinski, Donald R., et al; Replication Control and Other Stable Maintenance Mechanisms of Plasmids (1996) American Society for Microbiology Press, Washington, DC, pp. 2295-2324.
Herring, Christopher D., et al; Conditional Lethal Amber Mutations in Essential *Escherichia coli* Genes; Journal of Bacteriology (2004) vol. 186, No. 9 pp. 2673-2681.
Jacob, François., et al; Genetic Regulatory Mechanisms in the Synthesis of Proteins; Journal of Molecular Biology (1961) vol. 3 pp. 318-356.
Jensen, L. Bogø., et al; A Substrate-Dependent Biological Containment System for Pseudonomas Putida Based on the *Escherichia coli* gef Gene; Applied and Environmental Microbiology (1993) vol. 59, No. 11 pp. 3713-3717.
Jonasson,Per., et al; Genetic Design for Facilitated Production and recovery of Recombinant Proteins in *Escherichia coli*; Biotechnology Applied Biochemical (2002) vol. 35 pp. 91-105.
Kaplan, David L., et al; Streptavidin-based Containment Systems for Genetically Engineered Microorganisms; Biomolecular Engineering (1999) vol. 16 pp. 135-140.
Klemm, Per., et al; A Stochastic Killing System for Biological Containment of *Escherichia coli*; Applied and Environmental Microbiology (1995) vol. 61, No. 2 pp. 481-486.
Knudsen, Steen., et al; Development and Testing of Improved Suicide Functions for Biological Containment of Bacteria; Applied and Environmental Microbiology (1995) vol. 61, No. 3 pp. 985-991.
Kües, Ursula., et al; Replication of Plasmids in Gram-Negative Bacteria; Microbiological Reviews (1989) vol. 53, No. 4 pp. 491-516.
Lahijani, Roya., et al; High-Yield Production of pBR322-Derived Plasmids Intended for Human Gene Therapy by Employing a Temperature-Controllable Point Mutation; Human Gene Therapy (1996) vol. 7 pp. 1971-1980.
Li, Jing-Ya., et al; Characterization of Full Length and Truncated Type I Human Methionine Aminopeptidases Expresses from *Escherichia coli*; Biochemistry (2004) vol. 43 pp. 7892-7898.
Lin, E. C. C., et al; Bacteria, Plasmids, and Phages: An Introduction to Molecular Biology; (1984) Cambridge, Massachusetts: Harvard University Press, pp. 11-18.
Lin-Chao, Sue., et al; The Rate of Processing and Degradation of Antisense RNAI Regulates the Replication of ColEI-Type Plasmids in Vivo; Cell (1991) vol. 65 pp. 1233-1242.
Malmgren, Charlotta., et al; An Antisense/Target RNA Duplex or a Strong Intramolecular RNA Structure 5' of a Translation Initiation Signal Blocks Ribosome Binding: The Case of Plasmid R1; RNA (1996) vol. 2 pp. 1022-1032.
Merlin, Sean., et al; Assessment of Quantitative Models for Plasmid ColE1 Copy Number Control; J. Mol. Biol. (1995) vol. 248 pp. 211-219.

(Continued)

Primary Examiner — Nancy T Vogel
(74) Attorney, Agent, or Firm — Michael P. Morris; Edouard G. Lebel

(57) ABSTRACT

A host-vector system that uses the RNA-based copy number control mechanism of ColE1-type plasmids for regulating the expression of a marker gene allows for antibiotic-free selection of plasmids and is useful for production of plasmid DNA and recombinant proteins.

25 Claims, 11 Drawing Sheets

(56) References Cited

OTHER PUBLICATIONS

O'Kennedy, Ronan D., et al; Effects of Fermentation Strategy on the Characteristics of Plasmid DNA Production; Biotechnology Appl. Biochem. (2003) vol. 37 pp. 83-90.
O'Kennedy, Ronan D., et al; Effects of Growth Medium Selection on Plasmid DNA Production and Initial Processing Steps; Journal of Biotechnology (2000) vol. 76 pp. 175-183.
Postle, Kathleen., et al; Nucleotide Sequence of the Repressor Gene of the TN10 Tetracycline Resistance Determinant; Nucleic Acids Research (1984) vol. 12, No. 12 pp. 4849-4863.
Rawlings, Douglas E.; Proteic Toxin-Antitoxin, Bacterial Plasmid Addiction Systems and their evolution with Special reference to the pas System of pTF-FC2; FEMS Microbiology Letters (1999) vol. 176 pp. 269-277.
Reinikainen, P., et al; *Escherichia coli* Plasmid Production in Fermenter; Biotechnology Bioenginering (1988) vol. 33 pp. 386-393.
Ringquist, Steven., et al; Nature of the Ribosomal mRNA Track: Analysis of Ribosome-Binding Sites Containing Different Sequences and Secondary Structure; Biochemistry (1993) vol. 32 pp. 10254-10262.
Rogers, Mark., et al; Analysis of Tn7 Transposition; Molecular Gen. Genet (1986) vol. 205 pp. 550-556.
Ronchel, M. Carmen., et al; Characterization of Cell Lysis in Pseudomonas putida induced Upon Expression of Heterologous Killing Genes; Applied and environmental Microbiology (1998) vol. 64, No. 12 pp. 4904-4911.
Rouch, D. A., et al; Copper-Inducible Transcriptional Regulation at Two Promoters in the *Escherichia coli* Copper Resistance Determinant pco; Microbiology (1997) vol. 147 pp. 1191-1202.
Sano, Takeshi., et al; Recombinant Core Streptavidins; The Journal of Biological Chemistry (1995) vol. 270, No. 47 pp. 28204-28209.
Studier, F. William., et al; Use of Bacteriophage T7 RNA Polymerase to Direct Selective High-Level Expression of Cloned Genes; Journal Molecular Biology (1986) vol. 189 pp. 113-130.
Szafranski, Przemyslaw., et al; A New Approach for Containment of Microorganisms: Dual Control of Streptavidin Expression by Antisense RNA and the T7 Transcription System; Proc. Natl. Acad. Sci. USA (1997) vol. 94 pp. 1059-1063.
Tomizawa, Jun-Ichi., et al; Plasmid ColE1 Incompatibility Determined by Interaction of RNA I with Primer Transcript; Proc. Natl. Acad. Sci. USA (1981) vol. 78, No. 10 pp. 6096-6100.
Tomizawa, Jun-Ichi; Control of ColE1 Plasmid replication: The Process of Binding of RNA I to the Primer Transcript; Cell (1984) vol. 38 pp. 861-870.
Tomizawa, Jun-Ichi; Control of ColE1 Plasmid Replication: Binding of RNA I to RNA II and Inhibition of Primer Formation : Cell (1986) vol. 47 pp. 89-97.
Tomizawa, Jun-Ichi; Control of ColE1 Plasmid Replication: Intermediates in the Binding of RNA I and RNA II; Journal Molecular Biology (1990) vol. 212 pp. 683-694.
Tomizawa, Jun-Ichi ; Control of ColE1 Plasmid Replication: Interaction of Rom Protein with an Unstable Complex Formed by RNA I and RNA II; Journal Molecular Biology (1990) vol. 212 pp. 695-708.
Torres, Begoña., et al; As Gene Containment Strategy Based on a Restriction-Modification System; Environmental Microbiology (2000) vol. 2, No. 5 pp. 555-563.
Tsien, Roger Y.; The Green Fluorescent Protein; Annu. Rev. Biochem. (1998) vol. 67 pp. 509-544.
Vieira, Jeffrey., et al; The pUC Plasmids, an M13mp7-Derived System for Insertion Mutagenesis and Sequencing with Synthetic Universal Primers; Gene (1982) vol. 19 pp. 259-268.
Waddell, Candace S., et al; Tn7 Transposition: Two Transposition Pathways directed by Five Tn7-Encoded Genes; Genes & Development (1988) vol. 2 pp. 137-149.
Wang, Zhijun., et al; Medium Design for Plasmid DNA Production Based on Stoichiometric Model; Process Biochemistry (2001) vol. 36 pp. 1085-1093.

Williams, Steven G., et al; Repressor Titration: A Novel System for Selection and Stable Maintenance of Recombinant Plasmids; Nucleic Acids Research (1998) vol. 26, No. 9 pp. 2120-2124.
Yanofsky, Charles., et al; The Tryptophan Operon; American Society for Microbiology (1987) Washington, DC, pp. 1453-1472.
Yu, Daiguan., et al; An Efficient Recombination System for Chromosome Engineering in *Escherichia coli*; PNAS (2000) vol. 97, No. 11 pp. 5978-5983.
Zhang, Yanping, et al; Characterization of Chlorella Virus PBCV-1 CviAII Restriction and Modification System; Nucleic Acids Research (1992) vol. 20, No. 20 pp. 5351-5356.
Zuker, M., et al; Algorithms and Thermodynamics for RNA Secondary Structure Prediction: A Practical Guide: In RNA Biochemistry and Biotechnology (1999) pp. 11-43.
Chao, Michael Y., et al; RNALL Transcribed by IPTG-Induced T7 RNA Polymerase is Non-Functional as a Replication Primer for ColE1-Type Plasmids in *Escherichia coli*; Nucleic Acids Research (1995) vol. 23, No. 10 pp. 1691-1695.
Hiszczynska-Sawicka, Elzbieta., et al; effect of Integration Host Factor on RNA II Synthesis in Replication of Plasmid Containing orip15A; Plasmid (1998) vol. 40 pp. 150-157.
International Search Report for PCT/EP2005/054450 mailed Apr. 21, 2006.
Pichler, Silvia "Production of resistance-free plasmids for therapeutic use of DNA in human medicine" Diplom Thesis performed at the Institute for Applied Microbiology of the University for Soil Culture, Vienna, AT. Aug. 2002.
Bahl, Chnader P., et al; Minimal Length of the Lactose Operator Sequence for the Specific recognition by the Lactose Repressor; Proc. Natl. Acad. Sci. (1977) vol. 74 No. 3 pp. 966-970.
Balbas, Paulina et al; The Plasmid, pBR322; Biotechnology (1988) vol. 10 pp. 5-41.
Beck, Christoph F. et al; A Multifunctional Gene (tetR) controls Tn10-Encoded Tetracycline Resistance; Journal of Bacteriology, May 1982 pp. 633-642.
Bernard, Philippe., et al; Cell Killing by the F Plasmid CcdB Protein Involves Poisoning of DNA-Topoisomerase II Complexes; Journal of Molecular Biology (1992) vol. 226 pp. 735-745.
Bhagwat, Ashok S., et al; Structure and Properties of the region of Homology Between Plasmids pMB1 and ColE1; Mol. Gen Genet. (1981) vol. 182 pp. 505-507.
Bolivar, Francisco; Molecular Cloning Vectors Derived for the ColE1 Type Plasmid pMB1; Life Sciences (1979) vol. 25 pp. 807-818.
Brantl, Sabine "Antisense RNAs in plasmids: control of replication and maintenance" Academic Press, Plasmid 48 (2002) pp. 165-173.
Brosius, Jurgen., et al; Construction and Fine Mapping of Recombinant Plasmids Containing the rrnB Ribosomal RNA Operon of *E.coli*; Plasmid (1981) vol. 6 No. 1 pp. 112-118.
Brown, Eric D., et al; MurA (MurZ), The Enzyme that Catalyzes the First Committed Step in Peptidoglycan Biosynthesis, Is Essential in *Escherichia coli*; Journal of Bacteriology (1995) vol. 177 No. 14 pp. 4194-4197.
Cesareni, G., et al; Control of ColE1 Plasmid Replication by Antisense RNA; Trends Genet. (1991) vol. 7 No. 7 pp. 230-235.
Chan, Peter T., et al; Nucleotide Sequence and Gene Organization of ColE1 DNA; The Journal of Biological Chemistry (1985) vol. 260 No. 15 pp. 8925-8935.
Chang, Annie C. Y., et al; Construction and Characterization of Amplifiable Multicopy DNA Cloning Vehicles Derived for the P15A Cryptic Miniplasmid; Journal of Bacteriology (1978) vol. 134 No. 3 pp. 1141-1156.
Chang, Sheng-Yung P., et al; Methionine Aminopeptidase Gene of *Escherichia coli* Is Essential for Cell Growth; Journal of Bacteriology (1989) vol. 171 No. 7 pp. 4071-4072.
Chen, W., et al; Automated Fed-Batch Fermentation with Feed-Back Controls Based on Dissolved Oxygen (DO) and pH for Production of DNA Vaccines; Journal of.
Christoph F. Beck, et al; A Multifunctional Gene (tetR) Controls Tn10-encoded Tetracycline Resistance; Journal of Bacteriology (1982) vol. 150 No. 2 pp. 633-642.
Craig, Nancy; Mobile DNA; American Society of Microbiology (1989) pp. 1989 Washington D.C.

(56) References Cited

OTHER PUBLICATIONS

Cranenburgh, Rocky M. et al. "*Escherichia coli* strains that allow antibiotic-free plasmid selection and maintenance by repressor titration" Nucleic Acids Research, 2001 vol. 29, No. 5, 1-6.

Crozar, Anne., et al; Fusion of CHOP to a Novel RNA-Binding Protein in Human Myxoid Liposarcoma; Nature (1993) vol. 363 pp. 640-644.

Datsenko, Kirill A., et al; One-Step Inactivation of Chromosomal Genes in *Escherichia coli* K-12 Using PCR Products; PNAS (2000); vol. 97 No. 12 pp. 6640-6645.

Davison, John; Towards Safer Vectors for the Field Release of Recombinant Bacteria; Environ. Biosafety Research (2002) vol. 1 pp. 9-18.

Deboy, Robert T., et al; Target Site Selection by Tn7: attTn7 Transcription and Target Activity; Journal of Bacteriology (2000) vol. 182 No. 11 pp. 3310-3313.

Diaz, Ramon., et al; Origin and Direction of Mini-R1 Plasmid DNA Replication in Cell Extracts of *Escherichia coli*; Journal of Bacteriology (1982) vol. 150 No. 3 pp. 1077-1084.

Eguchi, Yutaka., et al; Complexes Formed by Complementary RNA Stem-loops. Their Formation, Structure and Interaction with ColE1 Rom Protein; Journal Molecular Biology (1991) vol. 220 pp. 831-842.

Eguchi, Yutaka; Antisense RNA; Annual Review Biochemistry (1991) vol. 60 pp. 631-652.

Eguchi, Yutska "Complex Formed by Complementary RNA Stem Loops and Its Stabilization by a Protein: Function of ColE1 Rom Protein" Cell Press vol. 60, 199-209 (1990).

Furste, Jens P., et al; Molecular Cloning of the Plasmid RP4 Primase Region in a Multi-Host-Range tacP Expression Vector; Gene (1986) vol. 48 pp. 119-131.

Gay, Philippe., et al; Cloning Structural Gene sacB, Which Codes for Exoenzyme Levansucrase of Bacillus subtilis: Expression of the Gene in *Escherichia coli*; Journal of Bacteriology (1983) vol. 153 No. 3 pp. 1424-1431.

Gerdes, Svetlana Y., et al; Experimental Determination and System Level Analysis of Essential Genes in *Escherichia coli* MG1655; Journal of Bacteriology (2003) vol. 185 No. 19 pp. 5673-5684.

Gerdes, Svetlana Y., et al; From Genetic Footprinting to Antimicrobial Drug Targets: Examples in Cofactor Biosynthetic Pathways; Journal of Bacteriology (2002) vol. 184 No. 16 pp. 4555-4572.

Gilbert, Walter., et al; The Nucleotide Sequence of the lac Operator; Proc. Natl. Acad. Sci. USA (1973) vol. 70 No. 12 pp. 3581-3584.

Mairhofer, Juergen et al., "A novel platform for the antibotic free maintenance of therapeutic plasmids" Congress Poster at Gene Vaccine Conference in Malaga, Spain 2007.

Mairhofer, Jürgen et al.; "A novel antibotic free plasmid selection system: Advances in safe and efficient DNA therapy" Biotechnology Journal (2008) 3, pp. 83-89.

Pfaffenzeller, Irene et al. "Using ColE1-derived RNA I for suppression of a bacterially encoded gene: implication for a novel plasmid addiction system" Biotechnology Journal (2006), pp. 1-7.

Camps, Manel "Modulation of ColE1-like Plasmid Replication for Recombinant Gene Expression" Recent Pat DNA Gene Seq. (2010) 4(1): 58-73.

Del Solar, Gloria et al. "Replication and Control of Ciruclar Bacterial Plasmids" Microbiolology and Molecular Biology Reviews (1998) vol. 62, No. 2, pp. 434-464.

Wang, Zhijun et al. "tRNA-dependent cleavage of the ColE1 plasmid-encoded RNA I" Microbiology (2006) 152, pp. 3467-3476.

\* cited by examiner

I)

II)

III)

SEQUENCE LISTING

```
<160> NUMBER OF SEQ ID NOS: 53

<210> SEQ ID NO 1
<211> LENGTH: 159
<212> TYPE: DNA
<213> ORGANISM: Artificial sequence
<220> FEATURE:
<223> OTHER INFORMATION: Primer

<400> SEQUENCE: 1
gaaattaata cgactcacta tagggaacaa aaaaaccacc gctaccagcg gtggtttgtt     60
tgcctctagt tcagctacca actgaaggag agaatacata tggctaaagg agaagaactt    120
ttcactggag ttgtcccaat tcttgttgaa ttagatggt                           159

<210> SEQ ID NO 2
<211> LENGTH: 161
<212> TYPE: DNA
<213> ORGANISM: Artificial sequence
<220> FEATURE:
<223> OTHER INFORMATION: Primer

<400> SEQUENCE: 2
gaaattaata cgactcacta tagggcctct agaaataatt ttgtttaact ttaagaagga     60
gatatacata tgcggatcaa gagctaccaa ctcttgttcc gatggctaaa ggagaagaac    120
ttttcactgg agttgtccca attcttgttg aattagatgg t                        161

<210> SEQ ID NO 3
<211> LENGTH: 45
<212> TYPE: DNA
<213> ORGANISM: Artificial sequence
<220> FEATURE:
<223> OTHER INFORMATION: Primer

<400> SEQUENCE: 3
gaaattaata cgactcacta tagggacagt atttggtatc tgcgc                     45

<210> SEQ ID NO 4
```

```
<211> LENGTH: 20
<212> TYPE: DNA
<213> ORGANISM: Artificial sequence
<220> FEATURE:
<223> OTHER INFORMATION: Primer

<400> SEQUENCE: 4
aacaaaaaaa ccaccgctac                                          20

<210> SEQ ID NO 5
<211> LENGTH: 45
<212> TYPE: DNA
<213> ORGANISM: Artificial sequence
<220> FEATURE:
<223> OTHER INFORMATION: Primer

<400> SEQUENCE: 5
gaaattaata cgactcacta tagggcaaa caaaaaaacc accgc                45

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
acagtatttg gtatctgcgc                                          20

<210> SEQ ID NO 7
<211> LENGTH: 23
<212> TYPE: DNA
<213> ORGANISM: Artificial sequence
<220> FEATURE:
<223> OTHER INFORMATION: Primer

<400> SEQUENCE: 7
gaaattaata cgactcacta tag                                      23

<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8
accatctaat tcaacaagaa ttg                                      23

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gatgatgcta gcaaaggaga agaac                                    25

<210> SEQ ID NO 10
<211> LENGTH: 27
<212> TYPE: DNA
<213> ORGANISM: Artificial sequence
<220> FEATURE:
<223> OTHER INFORMATION: Primer

<400> SEQUENCE: 10
```

```
gatgatggat ccttatttgt atagttc                                          27
```

<210> SEQ ID NO 11
<211> LENGTH: 122
<212> TYPE: DNA
<213> ORGANISM: Artificial sequence
<220> FEATURE:
<223> OTHER INFORMATION: Primer

<400> SEQUENCE: 11

```
taatacgact cactataggg gaattgtgag cggataacaa ttcccctcta gaaataattt      60
tgtttaactt aagaaggag atacatatgg gtaactggct tcagcagagc gcagatacca     120
tg                                                                   122
```

<210> SEQ ID NO 12
<211> LENGTH: 33
<212> TYPE: DNA
<213> ORGANISM: Artificial sequence
<220> FEATURE:
<223> OTHER INFORMATION: Primer

<400> SEQUENCE: 12

```
atcatcgcta gccatggtat ctgcgctctg ctg                                   33
```

<210> SEQ ID NO 13
<211> LENGTH: 123
<212> TYPE: DNA
<213> ORGANISM: Artificial sequence
<220> FEATURE:
<223> OTHER INFORMATION: Primer

<400> SEQUENCE: 13

```
taatacgact cactataggg gaattgtgag cggataacaa ttccccaaca aaaaaaccac      60
cgctaccagc ggtggtttgt ttgcctctag ttcagctacc aactgaagga gagaatacat    120
atg                                                                  123
```

<210> SEQ ID NO 14
<211> LENGTH: 31
<212> TYPE: DNA
<213> ORGANISM: Artificial sequence
<220> FEATURE:
<223> OTHER INFORMATION: Primer

<400> SEQUENCE: 14

```
atcatcgcta gccatatgta ttctctcctt c                                     31
```

<210> SEQ ID NO 15
<211> LENGTH: 119
<212> TYPE: DNA
<213> ORGANISM: Artificial sequence
<220> FEATURE:
<223> OTHER INFORMATION: Primer

<400> SEQUENCE: 15

```
gatgataagc tttaatacga ctcactatag gggaattgtg agcggataac aattcccctc      60
tagaaataat tttgtttaac tttaagaagg agatatacat atggctagca aaggagaag     119
```

<210> SEQ ID NO 16
<211> LENGTH: 32
<212> TYPE: DNA
<213> ORGANISM: Artificial sequence
<220> FEATURE:

<223> OTHER INFORMATION: Primer

<400> SEQUENCE: 16
gatgataagc tttaatacga ctcactatag gg        32

<210> SEQ ID NO 17
<211> LENGTH: 31
<212> TYPE: DNA
<213> ORGANISM: Artificial sequence
<220> FEATURE:
<223> OTHER INFORMATION: Primer

<400> SEQUENCE: 17
gatgatctcg agcaaaaaac ccctcaagac c        31

<210> SEQ ID NO 18
<211> LENGTH: 31
<212> TYPE: DNA
<213> ORGANISM: Artificial sequence
<220> FEATURE:
<223> OTHER INFORMATION: Primer

<400> SEQUENCE: 18
agtagtgaat tccaaaaaac ccctcaagac c        31

<210> SEQ ID NO 19
<211> LENGTH: 31
<212> TYPE: DNA
<213> ORGANISM: Artificial sequence
<220> FEATURE:
<223> OTHER INFORMATION: Primer

<400> SEQUENCE: 19
gatgatgcgg ccgcgttgcg acggtggtac g        31

<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20
gatgatgaat tctatgtttt taatcaaaca tcctg        35

<210> SEQ ID NO 21
<211> LENGTH: 33
<212> TYPE: DNA
<213> ORGANISM: Artificial sequence
<220> FEATURE:
<223> OTHER INFORMATION: Primer

<400> SEQUENCE: 21
gatgatctcg aggcatccat ttattactca acc        33

<210> SEQ ID NO 22
<211> LENGTH: 30
<212> TYPE: DNA
<213> ORGANISM: Artificial sequence
<220> FEATURE:
<223> OTHER INFORMATION: Primer

<400> SEQUENCE: 22
gatgatggta cctgaagaag ttcgcgcgcg        30

```
<210> SEQ ID NO 23
<211> LENGTH: 16
<212> TYPE: DNA
<213> ORGANISM: Artificial sequence
<220> FEATURE:
<223> OTHER INFORMATION: Primer

<400> SEQUENCE: 23
accggcgcag ggaagg                                                    16

<210> SEQ ID NO 24
<211> LENGTH: 18
<212> TYPE: DNA
<213> ORGANISM: Artificial sequence
<220> FEATURE:
<223> OTHER INFORMATION: Primer

<400> SEQUENCE: 24
tggcgctaat tgatgccg                                                  18

<210> SEQ ID NO 25
<211> LENGTH: 44
<212> TYPE: DNA
<213> ORGANISM: Artificial sequence
<220> FEATURE:
<223> OTHER INFORMATION: Primer

<400> SEQUENCE: 25
atgatgatgg cggccgcacc gacgctgatg gacagaatta atgg                     44

<210> SEQ ID NO 26
<211> LENGTH: 32
<212> TYPE: DNA
<213> ORGANISM: Artificial sequence
<220> FEATURE:
<223> OTHER INFORMATION: Primer

<400> SEQUENCE: 26
gctgctgagc tcccatcttt gattacggtg ac                                  32

<210> SEQ ID NO 27
<211> LENGTH: 29
<212> TYPE: DNA
<213> ORGANISM: Artificial sequence
<220> FEATURE:
<223> OTHER INFORMATION: Primer

<400> SEQUENCE: 27
atgatgctcg agcgccaaac gtgccactg                                      29

<210> SEQ ID NO 28
<211> LENGTH: 31
<212> TYPE: DNA
<213> ORGANISM: Artificial sequence
<220> FEATURE:
<223> OTHER INFORMATION: Primer

<400> SEQUENCE: 28
gctgctggta ccgaagtgaa caccagcctt g                                   31

<210> SEQ ID NO 29
<211> LENGTH: 19
<212> TYPE: DNA
<213> ORGANISM: Artificial sequence
<220> FEATURE:
<223> OTHER INFORMATION: Primer
```

<400> SEQUENCE: 29
ttcgggttcc agtaacggg                                                   19

<210> SEQ ID NO 30
<211> LENGTH: 19
<212> TYPE: DNA
<213> ORGANISM: Artificial sequence
<220> FEATURE:
<223> OTHER INFORMATION: Primer

<400> SEQUENCE: 30
tttcgaggta tcgccgtgg                                                   19

<210> SEQ ID NO 31
<211> LENGTH: 30
<212> TYPE: DNA
<213> ORGANISM: Artificial sequence
<220> FEATURE:
<223> OTHER INFORMATION: Primer

<400> SEQUENCE: 31
gctgctgagc tccaaagcgc gctaccagcg                                       30

<210> SEQ ID NO 32
<211> LENGTH: 40
<212> TYPE: DNA
<213> ORGANISM: Artificial sequence
<220> FEATURE:
<223> OTHER INFORMATION: Primer

<400> SEQUENCE: 32
atgatgatgg cggccgctta actgagaaca aactaaatgg                            40

<210> SEQ ID NO 33
<211> LENGTH: 33
<212> TYPE: DNA
<213> ORGANISM: Artificial sequence
<220> FEATURE:
<223> OTHER INFORMATION: Primer

<400> SEQUENCE: 33
atgatgctcg aggctcaaaa gccgttcagt ttg                                   33

<210> SEQ ID NO 34
<211> LENGTH: 31
<212> TYPE: DNA
<213> ORGANISM: Artificial sequence
<220> FEATURE:
<223> OTHER INFORMATION: Primer

<400> SEQUENCE: 34
gctgctggta cctgccagcg caactttgct c                                     31

<210> SEQ ID NO 35
<211> LENGTH: 19
<212> TYPE: DNA
<213> ORGANISM: Artificial sequence
<220> FEATURE:
<223> OTHER INFORMATION: Primer

<400> SEQUENCE: 35
gtacaaccgc caggtagtg                                                   19

<210> SEQ ID NO 36
<211> LENGTH: 20

```
<212> TYPE: DNA
<213> ORGANISM: Artificial sequence
<220> FEATURE:
<223> OTHER INFORMATION: Primer

<400> SEQUENCE: 36
gtctgattta tcagcgaggc                                              20

<210> SEQ ID NO 37
<211> LENGTH: 35
<212> TYPE: DNA
<213> ORGANISM: Artificial sequence
<220> FEATURE:
<223> OTHER INFORMATION: Primer

<400> SEQUENCE: 37
gctgctaagc ttgtcgacag ccactggagc acctc                             35

<210> SEQ ID NO 38
<211> LENGTH: 29
<212> TYPE: DNA
<213> ORGANISM: Artificial sequence
<220> FEATURE:
<223> OTHER INFORMATION: Primer

<400> SEQUENCE: 38
atgatgctcg agacggggag agcctgagc                                    29

<210> SEQ ID NO 39
<211> LENGTH: 30
<212> TYPE: DNA
<213> ORGANISM: Artificial sequence
<220> FEATURE:
<223> OTHER INFORMATION: Primer

<400> SEQUENCE: 39
atgatgggat ccaaaaggcc atccgtcagg                                   30

<210> SEQ ID NO 40
<211> LENGTH: 32
<212> TYPE: DNA
<213> ORGANISM: Artificial sequence
<220> FEATURE:
<223> OTHER INFORMATION: Primer

<400> SEQUENCE: 40
gtcgtcaagc ttataaaacg aaaggctcag tc                                32

<210> SEQ ID NO 41
<211> LENGTH: 30
<212> TYPE: DNA
<213> ORGANISM: Artificial sequence
<220> FEATURE:
<223> OTHER INFORMATION: Primer

<400> SEQUENCE: 41
gctgctggat ccgcgcccaa tacgcaaacc                                   30

<210> SEQ ID NO 42
<211> LENGTH: 37
<212> TYPE: DNA
<213> ORGANISM: Artificial sequence
<220> FEATURE:
<223> OTHER INFORMATION: Primer

<400> SEQUENCE: 42
```
atgatgatgg cggccgctgt gaaattgtta tccgctc         37

<210> SEQ ID NO 43
<211> LENGTH: 32
<212> TYPE: DNA
<213> ORGANISM: Artificial sequence
<220> FEATURE:
<223> OTHER INFORMATION: Primer

<400> SEQUENCE: 43
gctgctgaat tcataaaacg aaaggctcag tc              32

<210> SEQ ID NO 44
<211> LENGTH: 36
<212> TYPE: DNA
<213> ORGANISM: Artificial sequence
<220> FEATURE:
<223> OTHER INFORMATION: Primer

<400> SEQUENCE: 44
gctgctaagc ttgtcgacaa aaggccatcc gtcagg          36

<210> SEQ ID NO 45
<211> LENGTH: 35
<212> TYPE: DNA
<213> ORGANISM: Artificial sequence
<220> FEATURE:
<223> OTHER INFORMATION: Primer

<400> SEQUENCE: 45
gatgatgaat tctatgtttt taatcaaaca tcctg           35

<210> SEQ ID NO 46
<211> LENGTH: 29
<212> TYPE: DNA
<213> ORGANISM: Artificial sequence
<220> FEATURE:
<223> OTHER INFORMATION: Primer

<400> SEQUENCE: 46
gatgatgagc tcgttgcgac ggtggtacg                  29

<210> SEQ ID NO 47
<211> LENGTH: 33
<212> TYPE: DNA
<213> ORGANISM: Artificial sequence
<220> FEATURE:
<223> OTHER INFORMATION: Primer

<400> SEQUENCE: 47
gatgatctcg aggcatccat ttattactca acc             33

<210> SEQ ID NO 48
<211> LENGTH: 30
<212> TYPE: DNA
<213> ORGANISM: Artificial sequence
<220> FEATURE:
<223> OTHER INFORMATION: Primer

<400> SEQUENCE: 48
gatgatggta cctgaagaag ttcgcgcgcg                 30

<210> SEQ ID NO 49
<211> LENGTH: 35
<212> TYPE: DNA
<213> ORGANISM: Artificial sequence

```
<220> FEATURE:
<223> OTHER INFORMATION: Primer

<400> SEQUENCE: 49
gctgctgcta gcatgatgtc tagattagat aaaag                              35

<210> SEQ ID NO 50
<211> LENGTH: 36
<212> TYPE: DNA
<213> ORGANISM: Artificial sequence
<220> FEATURE:
<223> OTHER INFORMATION: Primer

<400> SEQUENCE: 50
gctgctggat ccttaagacc cactttcaca tttaag                             36

<210> SEQ ID NO 51
<211> LENGTH: 35
<212> TYPE: DNA
<213> ORGANISM: Artificial sequence
<220> FEATURE:
<223> OTHER INFORMATION: Primer

<400> SEQUENCE: 51
gtcgtcgaat tcttatttgt atagttcatc catgc                              35

<210> SEQ ID NO 52
<211> LENGTH: 116
<212> TYPE: DNA
<213> ORGANISM: Artificial sequence
<220> FEATURE:
<223> OTHER INFORMATION: Primer

<400> SEQUENCE: 52
gctgctaagc tttccctatc agtgatagag attgacatcc ctatcagtga tagagatact   60
gagcacatcg cggccgcttt aagaaggaga tatacatatg cgtaaaggag aagaac      116

<210> SEQ ID NO 53
<211> LENGTH: 24
<212> TYPE: DNA
<213> ORGANISM: Escherichia coli
<220> FEATURE:
<223> OTHER INFORMATION: Operator

<400> SEQUENCE: 53
tggaattgtg agcggataac aatt                                          24
```

HOST-VECTOR SYSTEM ANTIBIOTIC-FREE COLE1 PLASMID PROPAGATION

RELATED APPLICATIONS

This application is a continuation of U.S. Ser. No. 11/226,795, filed Sep. 14, 2005, which in turn claims priority from EP 04 022201 filed Sep. 17, 2004, each of which is hereby incorporated by reference in its entirety.

BACKGROUND AND DESCRIPTION OF THE INVENTION

The use of plasmid DNA as gene transfer vehicle has become widespread in gene therapy. In gene therapy applications, a plasmid carrying a therapeutic gene of interest is introduced into patients; transient expression of the gene in the target cells leads to the desired therapeutic effect.

Recombinant plasmids carrying the therapeutic gene of interest are obtained by cultivation of bacteria. For selecting bacterial transformants and in order to assure maintenance of the plasmids in the bacterial host cell, traditionally, an antibiotic resistance gene is included in the plasmid backbone. Selection for plasmids is achieved by growing the cells in a medium containing the respective antibiotic, in which only plasmid bearing cells are able to grow.

The use of antibiotic resistance genes for selection of plasmids for application in gene therapy is accompanied by severe drawbacks:

Since in gene therapy entire plasmids are being delivered, antibiotic resistance genes are introduced into the treated subject. Although these genes are driven by prokaryotic promoters and are should therefore not be active in mammalian cells and tissues, there is the chance that the delivered genes may be incorporated into the cellular genome and may, if in proximity of a mammalian promoter, become transcribed and expressed.

A second drawback of plasmids that bear antibiotic resistance genes is a potential contamination of the final product with residual antibiotic. In view of possible immune sensitization, this is an issue, especially in the case of beta-lactam antibiotics.

In order to avoid these risks, efforts have been made to ban antibiotic resistance genes from the manufacture of therapeutic plasmids and to develop alternative selection methods.

In an attempt to achieve antibiotic-free selection, plasmids have been used that can compensate a host auxotrophy. However, the main disadvantage of this and all related approaches is that additional genes on the plasmid are required (e.g. Hägg et al., 2004).

Another approach is a concept termed "repressor titration" (Wiliams et al., 1998). According to this concept, a modified *E. coli* host strain contains the kan gene (kanamycin resistance gene) under the control of the lac operator/promoter. In the absence of an inducer (IPTG or allolactose), the strain cannot grow on kanamycin-containing medium. Transformation with a high copy number plasmid containing the lac operator leads to kan expression by titrating lacI from the operator. Only cells that contain a high plasmid copy number are able to survive after addition of kanamycin. The major drawback of this concept is the fact that, again, the use of antibiotics is indispensable.

It has been an object of the invention to provide a novel system for selection of plasmids that goes without antibiotics.

To solve the problem underlying the invention, the mechanism of replication that is used by plasmids with a ColE1 origin of replication has been exploited. (In the following, plasmids with a ColE1 origin of replication are referred to as "ColE1-type plasmids".)

A large number of naturally occurring plasmids as well as many of the most commonly used cloning vehicles are ColE1-type plasmids. These plasmids replicate their DNA by using a common mechanism that involves synthesis of two RNA molecules, interaction of these molecules with each other on the one hand and with the template plasmid DNA on the other hand (Helinski, 1996; Kues and Stahl, 1989).

Representatives of ColE1-type plasmids are the naturally occurring ColE1 plasmids pMB1, p15A, pJHCMW1, as well as the commonly used and commercially available cloning vehicles such as pBR322 and related vectors, the pUC plasmids, the pET plasmids and the pBluescript vectors (e.g. Bhagwat and Person, 1981; Balbas et al., 1988; Bolivar, 1979; Vieira and Messing, 1982).

For all these plasmids, ColE1 initiation of replication and regulation of replication have been extensively described (e.g.: Tomizawa, 1981, 1984, 1986, 1989, 1990; Chan et al., 1985; Eguchi et al., 1991a; Cesareni et al., 1991). The ColE1 region contains two promoters for two RNAs that are involved in regulation of replication. Replication from a ColE1-type plasmid starts with the transcription of the preprimer RNA II, 555 bp upstream of the replication origin, by the host's RNA polymerase. During elongation, RNA II folds into specific hairpin structures and, after polymerization of about 550 nucleotides, begins to form a hybrid with the template DNA. Subsequently, the RNA II prepimer is cleaved by RNaseH to form the active primer with a free 3' OH terminus, which is accessible for DNA polymerase I (Lin-Chao and Cohen, 1991; Merlin and Polisky, 1995).

At the opposite side of the ColE1-type origin strand, RNA I, an antisense RNA of 108 nucleotides, complementary to the 5' end of RNA II, is transcribed. Transcription of RNA I starts 445 bp upstream from the replication origin, to approximately where the transcription of RNA II starts. RNA I inhibits primer formation and thus replication by binding to the elongating RNA II molecule before the RNA/DNA hybrid is formed.

The interaction of the two RNAs is a stepwise process, in which RNA I and RNA II form several stem loops. They initially interact by base-pairing between their complementary loops to form a so-called "kissing complex". Subsequently, RNA I hybridizes along RNA II, and a stable duplex is formed. Formation of the kissing complex is crucial for inhibition of replication. As it is the rate limiting step, is has been closely investigated (Gregorian and Crothers, 1995).

Apart from RNA I/RNA II interaction, the rom/rop transcript of ColE1 contributes to plasmid copy number control by increasing the rate of complex formation between RNA II and RNA I. To increase copy number, the gene encoding rom/rop has been deleted on some derivatives of pBR322, for example on pUC19.

The present invention relates, in a first aspect to a non-naturally occurring bacterial cell containing,
  i) a DNA sequence encoding a protein, the expression of which is to be regulated, and, operably associated thereto,
  ii) a DNA sequence encoding a RNA sequence that mimics a RNA II sequence, or parts thereof, and is complementary to a RNA I sequence that is transcribable from a plasmid with a ColE1 origin of replication.

In a further aspect, the present invention relates to a host-vector system comprising a plasmid with a ColE1 origin of replication and a bacterial host cell in which said plasmid can be replicated, wherein said host-vector system comprises a) a plasmid with a ColE1 origin of replication
b) a bacterial host cell in which said plasmid can be replicated, containing,
  i) a DNA sequence encoding a protein, the expression of which is to be regulated, and, operably associated thereto,
  ii) a DNA sequence encoding an RNA sequence that mimics an RNA II sequence, or parts thereof, and is complementary to an RNA I sequence that is transcribable from the plasmid a),
wherein said RNA sequence defined in ii), in the absence of the plasmid a), allows for expression of said protein and wherein, when said plasmid a) is present inside said host cell b), the RNA I molecule transcribed from the plasmid hybridizes with said RNA sequence defined in ii), whereby expression of said protein is suppressed.

In a preferred embodiment, the DNA sequence i) is a foreign DNA sequence.

In preferred embodiments, the protein encoded by said foreign DNA i) is toxic or lethal to the host cell.

In a further aspect, the present invention relates to a host-vector system comprising a plasmid with a ColE1 origin of replication and a bacterial host cell in which said plasmid can be replicated, wherein said host-vector system comprises
a) a plasmid with a ColE1 origin of replication,
b) a non-naturally occurring bacterial host cell containing, integrated in its genome,
  i) a foreign DNA sequence encoding a protein that is lethal or toxic to said host cell, and operably associated thereto
  ii) a DNA sequence encoding an RNA sequence that mimics an RNA II sequence, or parts thereof, and is complementary to an RNA I sequence transcribable from the plasmid a),
wherein said RNA sequence defined in ii), in the absence of the plasmid a), allows for expression of said lethal or toxic protein such that growth of said host cell is completely or partially inhibited and
wherein, when said plasmid a) is present inside said host cell, the RNA I molecule transcribed from the plasmid hybridizes with said RNA sequence defined in ii), whereby expression of said lethal or toxic protein is suppressed such that said complete or partial growth inhibition is abrogated in plasmid-bearing cells.

The invention makes use of the RNA-based copy number control mechanism of ColE1-type plasmids for regulating the expression of one or more genes that are present in the bacterial host cell, preferably inserted in the bacterial genome, and serve as selection markers.

In the following, the DNA sequence of i) (or the RNA transcribed from such DNA, respectively) is referred to as "marker gene" (or "marker RNA", respectively).

As mentioned above, in an embodiment of the invention, the marker gene encodes a protein that is lethal or toxic per se. In this embodiment, in the meaning of the present invention, the term "marker gene" also encompasses genes the expression of which results in a toxic effect that is not directly due to the expression product, but is based on other mechanisms, e.g. generation of a toxic substance upon expression of the marker gene. For simplicity, in the following, the protein encoded by the marker gene is termed the "marker protein"; in the case that the marker protein is a lethal or toxic protein, it is referred to as "toxic protein".

In a preferred embodiment, the marker protein is not lethal or toxic per se or due to a toxic effect generated upon its expression, but by repressing the transcription of a gene that is essential for growth of said bacterial cell. Such marker protein, or the DNA encoding it, respectively, is referred to as "repressor" or "repressor gene", respectively, and the gene that is essential for growth of the bacterial cells is referred to as "essential gene".

In the following, an RNA sequence that mimics an RNA II sequence, or parts thereof, is referred to as "RNA II-like sequence".

In the meaning of the present invention "operably associated" means that the DNA sequence i) and the DNA sequence ii) are positioned relative to each other in such a way that expression of the marker protein encoded by said DNA sequence i) is modulated by said RNA sequence ii) (the RNA II-like sequence).

The principle of the invention, i.e. RNA I-mediated marker gene down-regulation or silencing, is shown in FIG. 1:

The RNA II-like sequence is present on the host's transcript in combination with a Shine Dalgarno sequence. The RNA I sequence transcribed from the plasmid functions as an antisense RNA to said RNA II-like sequence and thus inhibits translation of the marker mRNA.

After induction of marker gene expression, in the case that the marker gene encodes a toxic protein, the host can only survive in the presence of the plasmid, because the plasmid provides the RNA I sequence that is complementary to the RNA II-like sequence and therefore hybridizes to the marker gene transcript, thus preventing the translation of the toxic protein. As described, regulation of the system is based on RNA-RNA interaction between the RNA I of the plasmid and, complementary thereto, an RNA II-like sequence of defined length that is positioned upstream or downstream the ribosomal binding site of the marker gene sequence, usually within the host's mRNA.

The length of the RNA II-like sequence and its distance and position relative to the ribosomal binding site and to the start codon of the marker gene must be such that the plasmid-free host is able to translate the mRNA; which means that care must be taken that the RNA II-like sequence does not interfere with ribosomal binding and translation.

Also, the inserted RNA II-like sequence must be designed and positioned such that it guarantees sufficient RNA-RNA interaction of the complementary sequences, so that when the plasmid is present, the RNA I transcribed therefrom binds to the mRNA of the host in an extent sufficient to inhibit translation of the marker gene. Inhibition of the marker gene must be to an extent such that an advantage in growth is provided, as compared to cells where no plasmid, hence no RNA I, is present.

Thus, the bacterial host is engineered such that in the absence of the ColE1-type plasmid the marker mRNA is translated into a marker protein, and in presence of a ColE1-type plasmid, translation of the protein is completely or partially suppressed. In the case that said mRNA encodes a toxic protein that partially or completely inhibits cell growth, hosts that contain the plasmid will survive the toxicity or outgrow plasmid-free hosts.

For the purpose of the present invention, a toxic protein is toxic in the sense that it partially or completely inhibits growth of the cells, at least to an extent to which cells without the marker gene have an advantage with regard to growth rate. If there are two populations of cells, on the one hand a population with the marker gene and, on the other hand, a population without or with an inhibited marker gene, in an equimolar distribution, the cell population without or with an inhibited marker gene will increase to 99% of the population in less than 10 generations.

In an embodiment of the invention, expression of the marker gene is regulated by an additional mechanism, e.g. by induction. Since in the case that the marker gene encodes a toxic protein, the marker gene needs to be turned off during cell propagation, an inducible promoter is advantageously used for transcriptional control, which promotes mRNA transcription only upon addition of an inducer. Examples are the T7 promoter in a T7-polymerase producing host, given that T7-polymerase is under control of the IPTG, or the lactose-inducible Lac-promoter, or an arabinose-inducible promoter.

Alternatively, said marker gene codes for a protein that is not per se toxic, but acts via an indirect mechanism, e.g. an enzyme, which, after addition of a substrate, modifies that substrate to a toxic substance. An example is SacB from *Bacillus subtilis*. sacB encodes a protein called levan sucrase. This protein turns sucrose into levan, a substance that is toxic to bacteria.

The RNA I sequence of the ColE1-type plasmid represents an essential feature that contributes to the advantages of the system. It provides selection criteria for plasmid-bearing hosts without the use of additional selection markers on the plasmid, e.g. antibiotic resistance genes. Thus, the invention provides an innovative system for antibiotic-free selection of ColE1-type plasmids.

In embodiments of the invention, the following components are useful:

1. Host Cells

Since their replication depends on the host machinery, ColE1-type plasmids are plasmids with a narrow host range. Replication is limited to *E. coli* and related bacteria such as *Salmonella* and *Klebsiella* (Kues and Stahl, 1989). Thus, the only mandatory property of the host is that it has the ability to replicate ColE1 plasmids. Suitable hosts are the widely used *Escherichia Coli* strains K12 or the B strain or related commercially available strains, e.g. JM108, TG1, DH5alpha, Nova Blue, XL1 Blue, HMS174 or L121 (for review see Casali, 2003).

Preferred genetic features of the host cell are mutations that improve plasmid stability and quality or recovery of intact recombinant protein. Examples of desirable genetic traits are recA (absence of homologous recombination), endA (absence of endonuclease I activity, which improves the quality of plasmid minipreps) or ompT (absence of an outer membrane protease), hsdr (abolished restriction but not methylation of certain sequences), hsdS (abolished restriction and methylation of certain sequences).

In the experiments of the invention, the host strain HMS174(DE3) (Novagen) was used, which contains the DE3 phage with the IPTG inducible T7 polymerase in its genome (Studier and Moffatt, 1986). Another example for a suitable host is HMS174(DE)pLysS, which additionally contains the pACYC184 plasmid (CmR) that carries the gene for the T7-lysozyme to decrease the transcriptional activity of the T7-Promoter in the un-induced state.

Particularly in the case of a lethal marker protein, it is desirable to avoid its expression without induction.

2. Constructs for Engineering the Host Cells

The principle of a construct suitable for engineering the host cells is shown in FIG. 2: All the components—two homologous arms [H], promoter+operator [P+O], RNA I marker sequence (RNA II-like sequence), marker gene [gene] (in the Examples, GFP was used in initial experiments) with a transcriptional terminator and the Kan cassette (kanamycin resistance cassette containing FRT, the +/−FLP recombinase recognition marker sequences; alternatively, other conventional selection markers may be used) are cloned into the multiple cloning site of a suitable vector, e.g. pBluescript KS+. Linear fragments for genomic insertion are cut out with restriction enzymes or amplified by PCR.

The kanamycin resistance cassette can be obtained, by way of example, from the pUC4K vector (Invitrogen). It can be cloned into the fragment at two different sites, namely before or after the marker gene. To avoid unintended premature transcription of the marker gene before it is turned on deliberately, the gene is preferably inserted in the opposite direction of the chromosomal genes.

Preferably, the marker construct is integrated in the bacterial genome. This can be achieved by conventional methods, e.g. by using linear fragments that contain flanking sequences homologous to a neutral site on the chromosome, for example to the attTN7-site (Rogers et al., 1986; Waddel and Craig, 1988; Craig, 1989) or to the recA site. Fragments are transformed into the host, e.g. *E. coli* strains MG1655 or HMS174 that contain the plasmid pKD46 (Datsenko and Wanner; 2000). This plasmid carries the λ Red function (γ, β exo) that promotes recombination in vivo. Alternatively, DY378 (Yu et al., 2000), an *E. coli* K12 strain which carries the defective λ prophage, can be used. In case of MG1655 or DY378 the chromosomal locus including the expression fragment can be brought into the HMS174(DE3) genome via transduction by P1 phage. Positive clones are selected for antibiotic resistance, e.g. in the case of using the Kan cassette for kanamycin, or chloramphenicol. The resistance genes can be eliminated afterwards using the FLP recombinase function based on the site-specific recombination system of the yeast 2 micron plasmid, the FLP recombinase and its recombination target sites FRTs (Datsenko and Wanner, 2000).

Alternatively to having the construct integrated in the host's genome, it may be present on a phage or a plasmid that is different from a ColE1-type plasmid and that is compatible with the system of the invention in the sense that it does not influence expression of the marker gene (and the gene of interest). Examples for suitable plasmids or phages are pACYC184 (which is a derivative of miniplasmid p15A; see Chang and Cohen, 1978), R1-miniplasmids (Diaz and Staudenbauer, 1982), F1-based plasmids or filamentous phages (Lin, 1984) or the plasmid pMMB67EH (Fürste et al., 1986) that was used in the experiments of the invention.

More specifically, the elements of suitable constructs can be defined as follows:

2.1. Homologous Arms

It was found in initial experiments of the invention that homologies of 30 bp on either side of the construct are sufficient for recombination by λ Red system (Yu, 2000). However, since better results are obtained with longer homologies, the arms are preferably in the range of 50-400 bp. In the Example homologous arms of 250 and 350 bp are used.

2.2. Promoter

If the foreign marker gene product is per se toxic or lethal to the cell or if it is a repressor, its expression has to be regulated. The promoter region has to contain suitable operator sequences (e.g. the Lac operator) that allow control of gene expression.

According to certain embodiments of the invention, the T7 promoter, the tac or the trc promoter, the lac or the lacUV5 promoter, the $p_{BAD}$ promoter (Guzman et al., 1995), the trp promoter (inhibited by tryptophan), the $P_1$ promoter (with $c_i$ repressor) or the gal promoter are used.

When using the lac operator, addition of IPTG (isopropyl thiogalactoside, an artificial inducer of the Lac operon) or lactose are used to activate the marker gene. When an inducible system is used, bacteria are able to survive without induction, but die upon addition of the inducer.

To achieve tight regulation of toxic gene expression, a tightly regulable promoter like the arabinose-inducible PBAD promoter (Guzman et al., 1995) is preferably used, in particular in the case that the marker protein is per se toxic to the cells.

Another way to control expression of the marker gene is by using constitutive promoters in combination with a gene that is non-toxic (e.g. a reporter gene) or only toxic under defined conditions, e.g. the *Bacillus subtilis* sacB gene. SacB is only toxic to *E. coli* when sucrose is present.

The promoter is chosen in coordination with the effect of the marker gene product and the required efficiency of down-regulation or silencing effect of RNA I. For example, for a construct containing a non-toxic or less toxic marker gene, a stronger promoter is desirable.

2.3. RNA II-Like Sequence

As RNA I has to act as a partial or complete inhibitor, RNA II-like sequences that are complementary to RNA I (10-555 nt) have to be presented upstream of the marker gene, together with a ribosome binding site (Shine-Dalgarno sequence) that is upstream, downstream or embedded within said RNA II-like sequence. Shine-Dalgarno sequence (SD) refers to a short stretch of nucleotides on a prokaryotic mRNA molecule upstream of the translational start site, that serves to bind to ribosomal RNA and thereby brings the ribosome to the initiation codon on the mRNA. When located upstream of the RNA II-like sequence, the SD sequence, preferably consisting of 7 nucleotides (GAAGGAG) should be located approximately 4 to 15 bp, e.g. 7 bp, upstream of the ATG start codon of the marker gene. In the case that a ribosome binding site is embedded within the RNA I sequence complementary to the marker gene, this sequence should be inserted such that only the stem region is altered, loop structures and preferably the whole secondary structure should stay intact in order to allow antisense RNA interaction with RNA I and formation of a kissing complex.

In an embodiment that provides a start codon in front of the RNAII-like sequence, the construct results in a fusion product comprising the marker sequence and the RNA II-like sequence.

In another embodiment, the RNA II-like sequence is inserted between the ribosomal binding site and the start codon; this approach is limited to the maximal gap possible to allow translation, e.g. 15 to 20 bp. (If the distance between the ribosomal binding site and the start codon increases, translational efficiency decreases.)

Alternatively to directly fusing the RNA II-like sequence and the marker gene, the RNA II-like sequence can be translationally coupled with the marker gene. To achieve this, by way of example, a construct may be used that starts with a start ATG, followed by the RNA II-like sequence, a further ribosome binding site, a sequence which represents an overlap between a stop and a start codon, e.g. TGATG, and the marker sequence. In this case the marker gene is only translated when the RNA II-like sequence has been translated before and separately from the marker gene. The advantage of this set up is that protein fusion to the marker gene is not required. This approach provides the option of separate translation, which may be beneficial for some marker proteins, e.g. in the case of some repressors like the Tet repressor.

Since even single RNA I/RNA II stem loops form kissing complexes (Eguchi 1991b; Gregorian, 1995), it has to be ensured that at least a single loop is formed. In any case, both requirements, i.e. on the one hand translation of the marker mRNA in spite of inserted loop structures and, on the other hand, efficient RNA-RNA antisense reaction between the inserted loop structure of the RNA II-like sequence and the complementary RNA I on the plasmid are fulfilled.

The interaction between RNA I and the marker mRNA that contains the RNA II-like sequence has the purpose to inhibit binding of the ribosome, thereby abolishing translation. Said mRNA is under control of an inducible promoter (e.g. the lac, arabinose or T7 promoter) and after induction (e.g. by IPTG, lactose, arabinose), expression of said marker gene is down-regulated, whenever sufficient RNA I is produced from the plasmid's origin of replication. Preferably, the marker gene encodes a lethal protein or a toxic protein that inhibits cell growth at least to a certain extent (as defined above); in this case, expression results in cell death or decreased cell growth (in plasmid-free cells), whereas down-regulation provides cell-growth (in plasmid-bearing cells).

Alternatively to marker genes that encode lethal or toxic proteins, the marker gene may encode any protein the expression of which is to be regulated during growth of bacterial cells, for whatever purpose. In particular, the marker gene may be a reporter gene, as described below (2.4.).

In the system of the present invention, RNA I, which is normally responsible for down-regulation of plasmid replication, acts as "gene-silencer", while inhibition of replication is decreased. Thus, the use of the system of the present invention results in an increase of plasmid replication, which is beneficial for survival of the bacterial host cells.

2.4. Marker Gene

RNA I-mediated down-regulation of the marker gene, which is a key feature of the invention, can be applied to any gene the expression of which, for any given purpose, is to be regulated.

According to a first aspect, RNA I-mediated down-regulation is useful for marker genes that are conditionally lethal to the host (e.g. see Davison, 2002, for review).

Examples for marker genes that are toxic per se and suitable in the present invention are genes encoding restriction nucleases (e.g. CviAII, a restriction endonuclease originating from *Chlorella* virus PBCV-1; Zhang et al., 1992), EcoRI (Torres et al., 2000), genes encoding toxins that interact with proteins, e.g. streptavidin or Stv13 (a truncated, easy soluble streptavidin variant), as described by Szafransky et al., 1997; Kaplan et al., 1999; Sano et al., 1995, which act by deprivation of biotin, an essential protein in cell growth); genes encoding proteins that damage membranes (the E gene protein of ΦX174 (Ronchel et al., 1998; Haidinger et al., 2002), gef (Jensen et al., 1993; Klemm et al., 1995), relF (Knudsen et al., 1995); genes that encode other bacterial toxins, e.g. the ccdb gene (Bernard and Couturier, 1992) that encodes a potent cell killing protein from the F-plasmid trapping the DNA gyrase or sacB from *Bacillus Subtilis* (Gay et al., 1983); or genes that encode eukaryotic toxins that are toxic to the bacterial host (e.g. FUS; Crozat et al., 1993). When using toxic genes, it is essential that their expression can be modulated by an inducible promoter. This promoter must not be active without inductor, but provide expression upon induction, sufficient to inhibit cell growth.

Further examples of genes toxic in bacteria and useful in the present invention are given by Rawlings, 1999.

In certain embodiments, the marker gene is selected from genes encoding restriction nucleases, streptavidin or genes that have an indirect toxic effect, e.g. SacB, as described above.

In a preferred embodiment, the toxic marker protein is not lethal or toxic per se or due to a toxic effect upon its expression, but a repressor protein which acts by repressing the transcription of a gene that is essential for growth of said bacterial cell.

In this embodiment of the invention, RNA I-mediated down-regulation in the presence of the plasmid affects the repressor. This means that the presence of RNA I and its interaction with the repressor mRNA (the RNA II-like sequence) leads to inhibition of the repressor and thus to activation or up-regulation of an essential gene, with the effect that growth of the cells only occurs in the presence of the replicating plasmid. In this embodiment, the promoter of an essential gene is modified by providing a binding DNA sequence (an "operator"), preferably the natural promoter is replaced by a complete, inducible promoter (containing an operator sequence) in such way that the expressed repressor protein, e.g. the Tet repressor, can bind to that operator, thereby inhibiting transcription and regulating expression of the essential gene, e.g. murA (by expression of the Tet repressor.).

The operator is a DNA sequence to which its specific repressor or enhancer is bound, whereby the transcription of the adjacent gene is regulated, e.g. the lac operator located in the lac promoter with the sequence TGGAATTGTGAGCG-GATAACAATT (SEQ ID NO: 53; Gilbert and Maxam, 1973) or derivatives thereof (Bahl et al., 1977). The repressor gene, which should not be present in the wild-type host, is engineered into the genome under the control of an inducible promoter, e.g. the T7, the lac or the tac promoter. Under normal growth conditions, the repressor is not expressed. After induction, by e.g. IPTG, the repressor is expressed, binds to the artificially introduced operator within the promoter region of the essential gene or the artificially inserted promoter and thus inhibits expression of the respective essential gene. Whenever there is replicating ColE1 plasmid present in the host, RNA I is produced which can bind to the repressor mRNA, which had been modified accordingly. By this RNA-RNA interaction, the translation of the repressor is inhibited (analogously to any other toxic marker protein). Consequently, the essential gene product can be produced and the cells maintain viable and grow.

In essence, in this embodiment the bacterial host comprises, besides the RNA II-like sequence, one of its essentials genes (as naturally embedded in the bacterial genome) under the control of an inducible promoter (which has been engineered into the genome to modify or, preferably completely replace the naturally occurring promoter of the essential gene). The promoter region controlling the essential gene also contains a DNA sequence (operator) that is recognized and specifically bound by said repressor protein. The repressor gene, which is engineered into the bacterial chromosome, is also under the control of an inducible promoter that is different from the promoter controlling the essential gene in thus independently inducible.

Essential bacterial genes are known from the literature, e.g. from Gerdes et al., 2002 and 2003, and from the PEC (Profiling the *E. coli* Chromosome) database (http://www.shigen.nig.ac.jp/ecoli/pec/genes.jsp), e.g. Isoleucyl-tRNA synthetase (ileS), cell division proteins like ftsQ, ftsA, ftsZ, DNA polymerase III alpha subunit (dnaE), murA, map, rpsA (30s ribosomal protein S1), rps B (30s ribosomal protein S2), lyt B (global regulator), etc.

A repressor is a protein that binds to an operator located within the promoter of an operon, thereby down-regulation transcription of the gene(s) located within said operon. Examples for repressors suitable in the present invention are the tetracyclin repressor (tet) protein TetR, which regulates transcription of a family of tetracycline resistance determinants in Gram-negative bacteria and binds to tetracyclin (Beck, et al., 1982; Postle et al., 1984), the tryptophan repressor (trp), which binds to the operator of the trp operon, which contains the tryptophan biosynthesis gene (Yanofski et al., 1987).

Examples for inducible promoters are promoters, where transcription starts upon addition of a substance, thus being regulable by the environment, e.g. the lac promoter, which is inducible by IPTG (Jacob and Monod, 1961), the arabinose-promoter (pBAD), inducible by arabinose (Guzman et al., 1995), and copper-inducible promoters (Rouch and Brown, 1997).

In the experiments of the invention, the tet-repressor (tetR) was chosen to be the repressor gene, which served as "toxic" marker gene by turning off an essential bacterial gene upon addition of the inducer IPTG.

For implementation of the repressor gene approach, two types of cassettes are designed and inserted in the bacterial chromosome in the experiments of the invention (Example 4). The first set of constructs comprises cassettes that serve to replace (or modify) promoters of specific essential genes on the genome. The second type of cassettes serve as test constructs employing GFP as a surrogate for an essential gene to provide proof of concept. The aim of the experiments using the GFP test constructs is to evaluate regulatory cascades, promoter strengths and thus adjustment of all interacting components of the system.

Thus, in another embodiment, the marker gene is a reporter gene, e.g. encoding GFP (Green Fluorescent Protein), hSOD (human superoxide dismutase), CAT (chloramphenicol acetyltransferase) or luciferase.

A reporter gene is useful in cultivation processes whenever information on the presence or absence of a ColE1-type plasmid in a host cell or on plasmid copy number is needed. Such information is particularly useful when fermentation processes are to be optimized with regard to control of plasmid copy number.

A reporter gene may also serve as a surrogate of a toxic marker gene, and may thus be used in experimental settings that aim at proving the functionality of constructs to be employed for the gene-regulating or silencing and to determine their effect on a toxic marker gene.

In order to evaluate the functionality of constructs designed for engineering a bacterial host such that expression of a toxic marker gene can by regulated by a ColE1-type plasmid, the reporter gene "green fluorescent protein" (GFP) served as a model in the initial experiments of the invention. Due to its auto-fluorescence (Tsien, 1998) GFP was considered suitable to substitute the marker gene, or the essential gene, respectively, in the initial experiments.

In certain embodiments of the invention, the marker gene may be an endogenous host gene, which may be any gene of interest that is intended to be regulated. In this case, the host cell is engineered such that the sequence encoding the RNA II-like sequence is operably associated with the relevant host gene, as described in 2.3.

3. ColE1-Type Plasmid

In the present invention, all ColE1-type plasmids with their natural RNA I/RNA II pairs, as well as with modified RNA I and/or RNA II sequences, e.g. as described in WO 02/29067, may be used.

As mentioned above, representatives of useful ColE1-type plasmids are the naturally occurring ColE1 plasmids pMB1, p15A, pJHCMW1, as well as the commonly used and commercially available cloning vehicles such as pBR322 and related vectors, the pUC plasmids, the pET plasmids and the pBluescript vectors.

No antibiotic resistance genes need to be included in the plasmid sequence. As essential elements, the plasmid basically only contains the ColE1 origin of replication and the gene expression cassette carrying the gene of interest.

The gene of interest on the plasmid and its promoter depend on the type of application; the invention is not limited in any way with respect to the gene of interest, e.g. a therapeutic gene. For gene therapy applications, the gene may be operably associated to an eukaryotic promoter, e.g. the CMV promoter.

APPLICATION OF THE INVENTION

The present invention can be widely used in state-of-the-art fermentations, both for plasmid DNA production and for producing recombinant proteins.

Several approaches for fermentation of pDNA have been described that are useful for applying the present invention. The methods for plasmid DNA production differ with regard to the level of control imposed upon the cells and the numerous factors that influence fermentation:

For pDNA production on a laboratory scale, cultivation of plasmid-bearing cells in shake flasks is the simplest method (O'Kennedy et al., 2003; Reinikainen et al., 1988; O'Kennedy et al., 2000; U.S. Pat. No. 6,255,099).

To obtain higher quantities of plasmids, the cells can be cultivated in controlled fermenters in so-called "batch fermentations", in which all nutrients are provided at the beginning and in which no nutrients are added during cultivation. Cultivations of this type may be carried out with culture media containing so called "complex components" as carbon and nitrogen sources, as described e.g. by O'Kennedy et al., 2003, and Lahijani et al., 1996, and in WO 96/40905, U.S. Pat. No. 5,487,986 and WO 02/064752. Alternatively, synthetic media may be used for pDNA production, e.g. defined culture media that are specifically designed for pDNA production (Wang et al., 2001; WO 02/064752).

The present invention may also be used in fed batch fermentations of $E.\ coli$, in which one or more nutrients are supplied to the culture by feeding, typically by using a feed-back control algorithm by feeding nutrients in order to control a process parameter at a defined set point. Feed-back control is hence directly related to cell activities throughout fermentation. Control parameters which may be used for feed-back control of fermentations include pH value, on line measured cell density or dissolved oxygen tension (DOT). A feed-back algorithm for controlling the dissolved oxygen tension at a defined set point by the feeding rate was described in WO 99/61633.

Another, more complex algorithm uses both the DOT and the pH value as control parameters for a feed-back cultivation method (U.S. Pat. No. 5,955,323; Chen et al., 1997).

Another feeding mode is based on the supply of feeding medium following an exponential function. The feeding rate is controlled based on a desired specific growth rate $\mu$. WO 96/40905 and O'Kennedy et al., 2003 describe methods that use an exponential fed-batch process for plasmid DNA production. Lahijani et al., 1996, describe combining exponential feeding with temperature-controllable enhancement of plasmid replication.

Alternatively, the invention may be applied in a process for producing plasmid DNA, in which $E.\ coli$ cells are first grown in a pre culture and subsequently fermented in a main culture, the main culture being a fed-batch process comprising a batch phase and a feeding phase. The culture media of the batch phase and the culture medium added during the feeding phase are chemically defined, and the culture medium of the feeding phase contains a growth-limiting substrate and is added at a feeding rate that follows a pre-defined exponential function, thereby controlling the specific growth rate at a pre-defined value.

When the marker gene is under the control of an inducible promoter, the inducer may be added to the batch at the beginning and/or pulse-wise (both in a batch and in fed-batch cultivations). During the feed phase, the inducer may be added pulse-wise or continuously.

At the end of the fermentation process, the cells are harvested and the plasmid DNA is isolated and purified according to processes known in the art, e.g. by methods based on anion exchange and gel permeation chromatography, as described in U.S. Pat. No. 5,981,735 or by using two chromatographic steps, i.e. an anion exchange chromatography as the first step and reversed phase chromatography as the second step, as described in U.S. Pat. No. 6,197,553. Another suitable method for manufacturing plasmid DNA is described in WO 03/051483, which uses two different chromatographic steps, combined with a monolithic support.

In addition to applying the invention for plasmid production, e.g. for production of plasmids for gene therapy applications, it is also useful for recombinant protein production.

With regard to recombinant protein production, in principle, any method may be used that has proven useful for expressing a gene of interest in $E.\ coli$, in particular from a ColE1 type plasmid (see, for review, e.g. Jonasson et al., 2002; Balbas, 2001). The protein may be obtained intracellularly (completely or partially soluble or as inclusion bodies) or by secretion (into the cell culture medium or the periplasmic space) from batch fermentations or, preferably, fed-batch cultivations, using complex, synthetic or semisynthetic media.

In plasmid DNA production, usually plasmid DNA for gene therapy applications, the gene of interest is not expressed in the bacterial host cell. In view of its application in mammals, preferably in humans, where it is to be ultimately expressed, the gene of interest is usually operably associated with a eukaryotic promoter. In contrast, for recombinant production of proteins in $E.\ coli$, the gene of interest is to be expressed in the host cell therefore under the control of a prokaryotic promoter.

For recombinant protein production, the two promoters, i.e. the promoter controlling the marker gene and the promoter controlling the gene of interest, may be different or the same, as long as no interference occurs that disturbs expression of either one.

Advantageously, since their activity is independent of each other concerning time-point and level of transcription, the promoters are differently regulated. Preferably, the promoter controlling the marker gene is active at the start of the fermentation process and produces moderate amounts of mRNA, while the promoter of the gene of interest is rather strong and activated at a chosen time-point during fermentation. If inducible promoters are used for both the gene of interest and the marker gene, they are usually chosen such that they are turned on by different inducers. Alternatively, the marker gene may be under an inducible and the gene of interest under a constitutive promoter, or vice versa. This applies both for methods in which the marker gene construct is integrated in the bacterial host genome and in which the marker gene construct is contained in a plasmid or phage, as described above.

With regard to induction of the promoter in the various phases of fermentation, the principle described above for plasmid DNA production applies.

The invention has the great advantage that all replicated plasmids are devoid of antibiotic resistance genes and are therefore, in addition to gene therapy applications, suitable for all applications for which the absence of antibiotic resistance genes is required or desirable, e.g. for the generation of recombinant yeast strains that are intended for human and animal food production or for the generation of recombinant plants.

Figure 4:
FIG. 4: Constructs containing marker gene and RNA II-like sequences
Figure 4:
Figure 4:

(equivalent to III in FIG. 4), the oligonucleotide of SEQ ID NO: 2 contains loop 2 of RNA I (equivalent to II in FIG. 4).

Oligonucleotides of SEQ ID NO: 3 and 4 are used to amplify RNA I (110 bp) from a ColE1 plasmid and to incorporate the T7 promoter for in vitro transcription. Oligonucleotides of SEQ ID NO: 5 and 6 are used to amplify RNA I (110 bp) from a ColE1 plasmid and to incorporate the T7 promoter for in vitro transcription. Oligonucleotides of SEQ ID NO: 7 and 8 are also used to produce DNA for the negative control (equivalent to I in FIG. 4) from pet11aGFP as template. Negative control is a fragment of the green fluorescent protein mRNA in context with the T7 promoter and a ribosomal binding site.

EXAMPLE 1

Hybridization Experiments with In Vivo Transcribed Constructs

In order to chose the desired length and position of the sequence complementary to RNA I (the RNA II-like sequence), within the mRNA molecule the translation of which is to be inhibited by hybridization, in vitro antisense experiments are carried out. RNA hybrids of RNA I to different synthetic RNAs and to RNA II are subjected to a gel shift assay.

TABLE 1

| Org. | SEQ ID NO: | Primer | Length | Sequence |
|---|---|---|---|---|
| (T7, E. coli, A. victoria) | 1 | T7 rbs@st-loop2 + 1 | 159 mer | 5'GAAATTAATACGACTCACTATAGG GAACAAAAAAACCACCGCTACCAGC GGTGGTTTGTTTGCCTCTAGTTCAGC TACCAACTGAAGGAGAGAATACATA TGGCTAAAGGAGAAGAACTTTTCAC TGGAGTTGTCCCAATTCTTGTTGAAT TAGATGGT 3' |
| (T7, E. coli, A. victoria) | 2 | T7-atg-loop2-sbulge | 161 mer | 5'GAAATTAATACGACTCACTATAGG GCCTCTAGAAATAATTTTGTTTAACT TTAAGAAGGAGATATACATATGCGG ATCAAGAGCTACCAACTCTTGTTCCG ATGGCTAAAGGAGAAGAACTTTTCA CTGGAGTTGTCCCAATTCTTGTTGAA TTAGATGGT 3' |
| T7, E. coli | 3 | T7Prom-sRNA I_ColEI-back | 45 mer | 5'GAAAT*TAATACGACTCACTATAGGG* ACAGTATTTGGTATCTGCGC 3' |
| E. coli | 4 | asRNA I_ColEI- for | 20 mer | 5' AACAAAAAAACCACCGCTAC 3' |
| T7, E. coli | 5 | T7Prom-RNA IIse_ColEI-back | 45 mer | 5'GAAAT*TAATACGACTCACTATAGGG* GCAAACAAAAAAACCACCGC 3' |
| E. coli | 6 | RNA IIse_ColEI-for | 20 mer | 5'ACAGTATTTGGTATCTGCGC 3' |
| T7, E. coli | 7 | oligo-T7prom-p11a-back | 23 mer | 5'GAAATTAATACGACTCACTATAG 3' |
| A. victoria | 8 | oligo-GFP-for | 23 mer | 5'ACCATCTAATTCAACAAGAATTG 3' |

The oligonucleotides of SEQ ID NO: 1 and 2 containing the RNA-I complementary sequence in the context with the T7 promoter and ribosomal binding site, and the first 60 nucleotides of the GFP cDNA, are amplified using oligonucleotide of SEQ ID NO: 7 and 8 and used for in vitro transcription by T7 polymerase (see Example 1). Oligonucleotide of SEQ ID NO: 1 contains loop 1 and loop 2 of RNA I To this end, artificially designed GFP constructs that contain an RNA II-like sequence are transcribed in vitro and incubated with in vitro transcribed RNA I. Hybridization is detected on native RNA-polyacrylamide gels.

Figure 1:
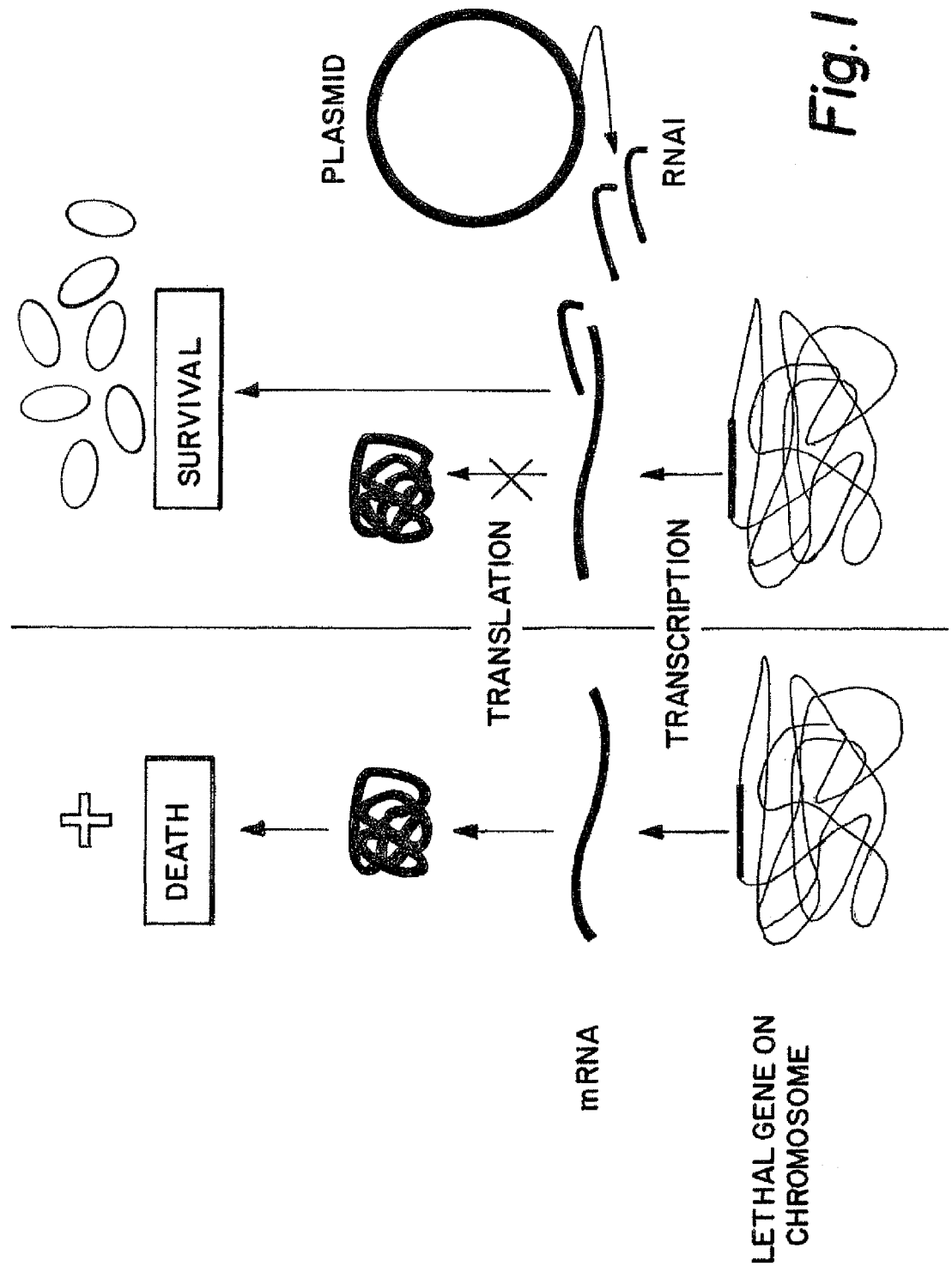
FIG. 1: Principle of RNA I-mediated marker gene down-regulation or silencing
Figure 2:
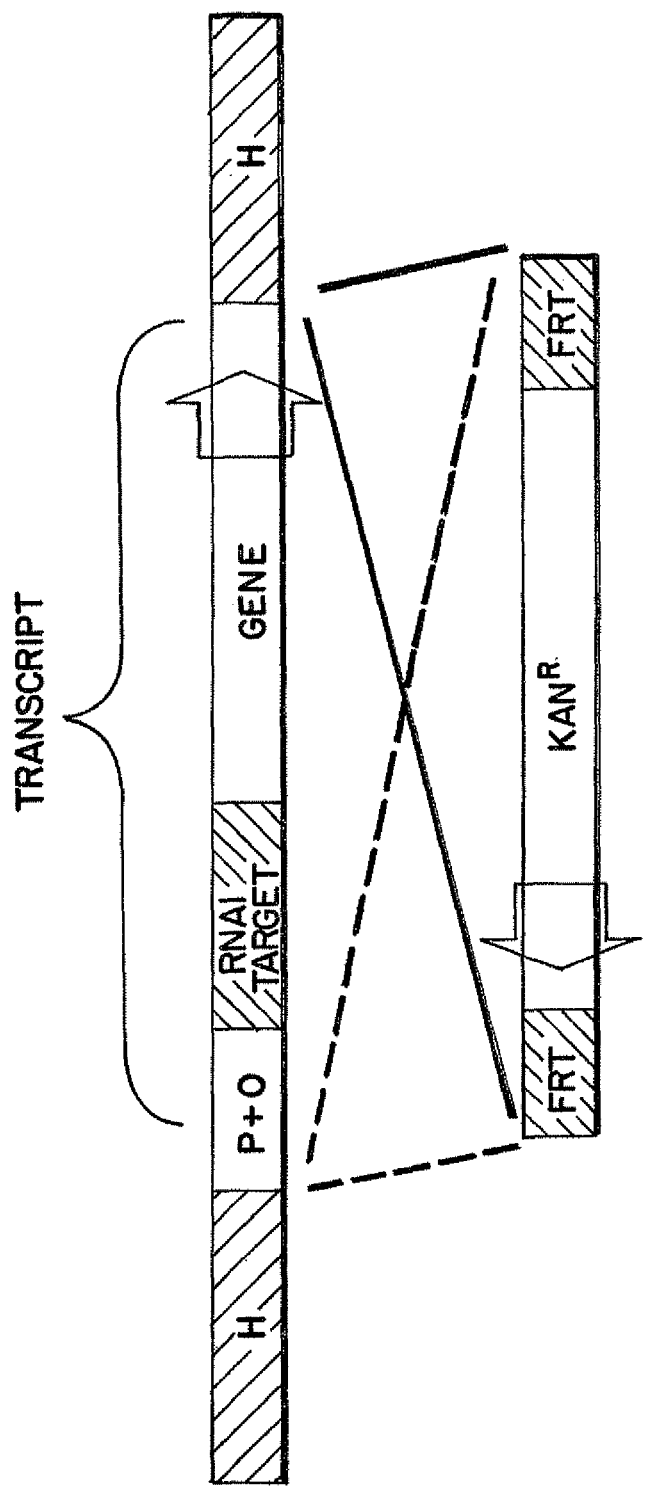
FIG. 2: Construct for engineering host cells

Synthetic RNAs (RNA I and synthetic constructs with RNA II hairpin structures at their 5' end) are obtained by in vitro transcription (Ampliscribe, T7-Flash Transcription Kit;

Epicentre) (FIG. 2). 110 bp of RNA I and RNA II each from pBR322 ori and oligonucleotides (oligonucleotides SEQ ID NO: 1 and 2) obtained from Metabion are amplified by PCR and serve as linear DNA templates for in vitro transcription.

To verify RNA I and RNA II-target interactions, gel shift experiments are carried out. Loop-loop complexes are visualised as they appear retarded.

RNAs are heated separately, prior to hybridization. Gels are 75 mm thick, 5% (w/v) polyacrylamide (60:1) and are run in a mini protein gel apparatus (Pharmacia) cooled with ice cold water. The running buffer is 1× Tris-borate (89 mM Tris (pH 8.3), 89 mM boric acid) containing 5 mM $MgCl_2$. Bands are stained with ethidium bromide and viewed using a UV transilluminator.

Figure 3:
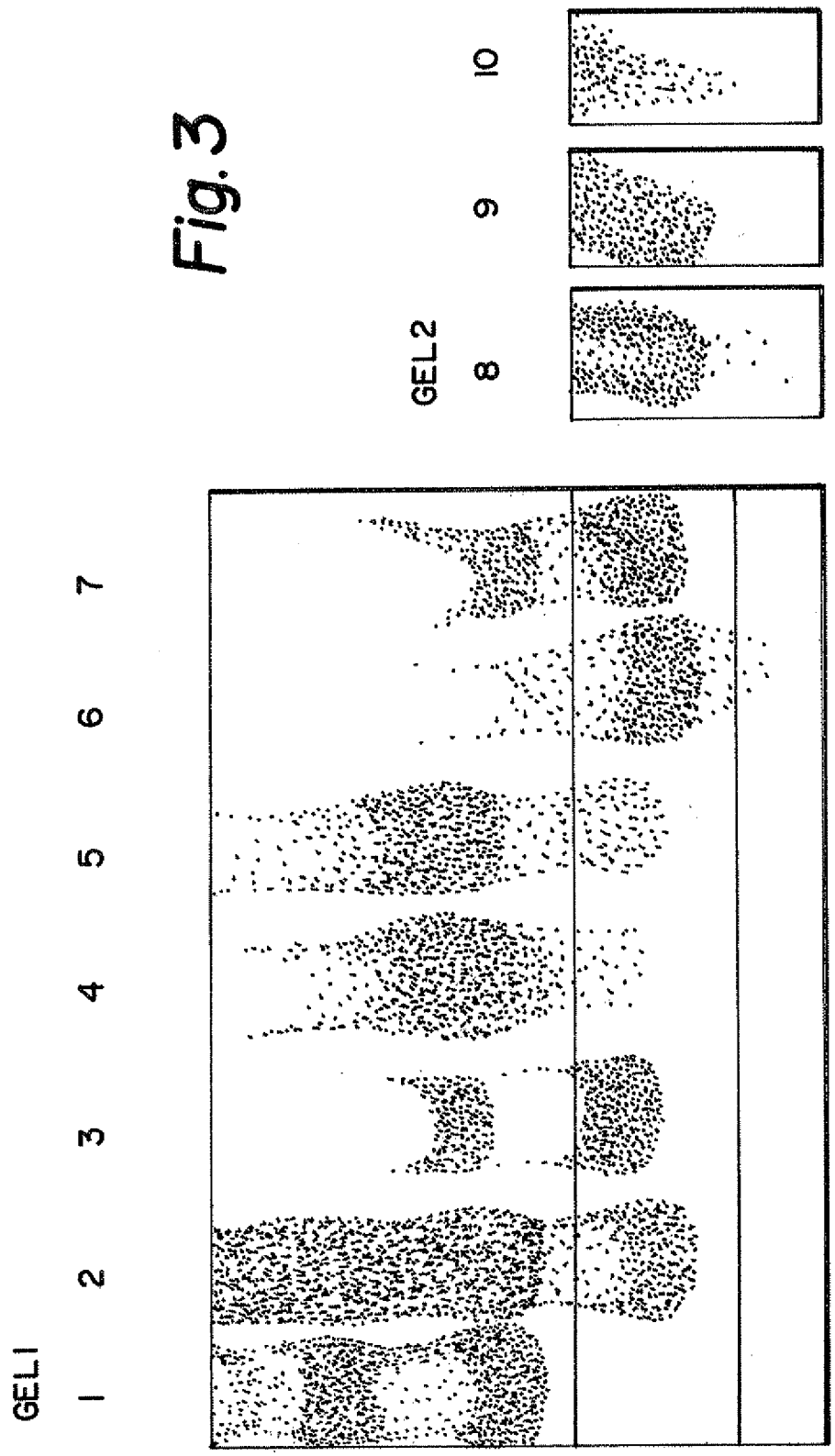
FIG. 3: Results from hybridization experiments with in vivo transcribed constructs

When 60 nt of GFP mRNA including RBS and start codon with and without RNAII sequences at the beginning of the transcripts are incubated with RNAI, the results shown in FIG. 3 are obtained.

Gel 1 of FIG. 3 shows positive ($RNAII108$ nt, corresponding to the complete RNAI sequence and negative control. If a reaction has occurred between the two RNAs, the (marked) RNAI band appears weaker, because it is retarded.

Gel 1:
1 neg. control RNA
2. RNAI+neg. control RNA
3 $RNAII_{108nt}$
4 RNAI+$RNAII_{108nt}$ (heating prior to incubation (3 min at 90° C.)
5 RNAI+$RNAII_{108nt}$
6 RNAI (heating prior to incubation (3 min at 90° C.))
7 RNAI On gel 2 of FIG. 3, lanes 8, 9 and 10, only the RNAI band is shown. When incubated with a transcript carrying one RNAII loop, a very weak reaction is seen, whereas a transcript with two loops gave a strong reaction.

Gel 2:
8 RNAI
9 RNAI (+RNAII loop2)
10 RNAI (+RNAII loop1 and 2)

Loop2GFP (lane 9) shows a slightly weakened RNA I band compared to the negative control, whereas Loop 1+2GFP (lane 10) shows a dramatic decrease in the RNA I band, indicating formation of a kissing complex. This data shows that RNA-RNA interaction with the presence of only one loop is efficient.

Loop constructs that indicate formation of a kissing complex on the gel—even a weak one—are cloned into pMMB67EH and pBluescriptII KS+ and tested for GFP expression. Since interaction of RNA I with a marker containing two hairpin loops is stronger, this construct is considered the favorite candidate for the in vivo experiments.

EXAMPLE 2

In Vivo Assay to Test Gene Expression and Gene Silencing

In the constructs to be tested, either one or two RNA II stem loops are cloned into an expression vector. Secondary structures and proper folding of the transcript are confirmed by the computer program RNAfold (Gene Quest, Vienna RNA folding procedure; see Zuker, 1999). For this experiment, an expression vector with a non-ColE1 origin, for example pMMB67EH (Fürste et al., 1986) is considered useful to circumvent RNA I-target interactions within the plasmid and to determine whether GFP expression is hampered by the presence of additional sequences in proximity of the ribosomal binding site. This is considered to be an important point, because additional sequences and secondary structures on or near the ribosomal track usually decrease or even completely inhibit gene expression (Malmgren, 1996; Ringquist, 1993).

Based on the results obtained with the native RNA gels (see Example 1), two fusions of GFP with RNA II-like sequences are constructed (FIG. 4). Two different RNA II-like sequences are inserted upstream of the GFP coding sequences, under control of the T7 promoter and lac operator.

The gfp gene is amplified from pGFPmut3.1 by primers NheI-GFP-back and BamHI-GFP-for (for primer sequences see Table 2). The T7/lacO promoter—with and without RNAII loops/RBS combinations—is fully synthesized on primers (HindIII-T7GFP-back) and together with BamHI-GFP-for used to amplify gfp or synthesized on oligos (T7al3-oligo and T7L12ras-oligo) and fused to the amplified gfp by NheI restriction site. The whole fragment is cloned into pMMB67EH by BamHI and HindIII restriction (for primers and oligos see Table 2).

TABLE 2

Selected constructs

| Org. | SEQ ID NO: | Primer/Oligo | Sequence |
|---|---|---|---|
| A. victoria | 9 | NheI-GFP-back | 5' GAT GAT GCT AGC AAA GGA GAA GAA C 3' |
| A. victoria | 10 | BamHI-GFP-for | 5' GAT GAT GGA TCC TTA TTT GTA TAG TTC 3' |
| (T7, E. coli) | 11 | T7al3-oligo | 5' TAA TAC GAC TCA CTA TAG GGA ATT GTG AGC GGA TAA CAA TTT CCC CTC TAG AAA TAA TTT TGT TTA ACT TTA AGA AGG AGA TAC ATA TGG GTA ACT GGC TTC AGC AGA GCG CAG ATA CCA TG 3' |
| E. coli | 12 | Nhe-ATG-loop3-for | 5' ATC ATC GCT AGC CAT GGT ATC TGC GCT CTG CTG 3' |
| (T7, E. coli) | 13 | T7L12ras-oligo | 5' TAA TAC GAC TCA CTA TAG GGA ATT GTG AGC GGA TAA CAA TTT CCC CAA CAA AAA AAC CAC CGC TAC CAG CGG TGG TTT GTT TGC |

TABLE 2-continued

Selected constructs

| Org. | SEQ ID NO: | Primer/Oligo | Sequence |
|---|---|---|---|
| | | | CTC TAG TTC AGC TAC CAA CTG AAG GAG AGA ATA CAT ATG 3' |
| artificial | 14 | Nhe-ras12 for | 5' ATC ATC GCT AGC CAT ATG TAT TCT CTC CTT C 3' |
| T7, E. coli, A. victoria | 15 | HindIII-T7GFP-back | 5' GAT GAT AAG CTT TAA TAC GAC TCA CTA TAG GGG AAT TGT GAG CGG ATA ACA ATT CCC CTC TAG AAA TAA TTT TGT TTA ACT TTA AGA AGG AGA TAT ACA TAT GGC TAG CAA AGG AGA AG 3' |
| T7 | 16 | HindIII-T7-back | 5' GAT GAT AAG CTT TAA TAC GAC TCA CTA TAG GG 3' |
| T7 | 17 | XhoI-T7term-for | 5' GAT GAT CTC GAG CAA AAA ACC CCT CAA GAC C 3' |
| T7 | 18 | EcoRI-T7term-for | 5' AGT AGT GAA TTC CAA AAA ACC CCT CAA GAC C 3' |

The constructs are cloned into the pMMB67EH vector to confirm GFP expression in spite of additional sequences in proximity to the ribosomal binding site. Both constructs produce GFP, but expression is significantly lower as compared to a construct without hairpin loops. The two constructs are cloned into vector pBluescript containing the Tn7 homologies and the kanamycin resistance gene, which serves for selection of hosts that have the capacity to integrate the entire cassette into the chromosome. The GFP cassettes are inserted on the bacterial chromosome as described before.

FIG. 4: shows constructs that are cloned into pMMB67EH and also inserted on the genome of HMS174(DE3). Cassettes for I) HMS174(DE3)T7GFP=IS5, II) HMS174(DE3) T7aL3GFP=IS11 and III) HMS174(DE3) T7112rasGFP=IS13

As T7aL3GFP and T7112rasGFP show GFP expression when cloned into pMMB67EH, these expression cassettes—and T7GFP as a negative control—are inserted on the bacterial chromosome for testing their ability to serve as a target for antisense RNAI. The constructs are cloned into vector pBluescript KSII+ by BamII and HindIII restriction sites. The Tn7 homologies are amplified from *E. coli* HMS174(DE3) colonies with primers NotI-Tn7/1-back and EcoRI-Tn7-for homology 1 and primers XhoI-Tn7/2-back and KpnI-Tn7-for homology 2 (for primer sequences see Table 3). For the kanamycin resistance cassette, which serves for selection of hosts that have the entire cassette integrated into the chromosome, the EcoRI fragment from pUC4K is taken. The T7 Terminator is amplified from expression vector pET11a by primers XhoI-T7term-for and EcoRI-T7 term-for (Table 2). The entire plasmids are digested by NotI and KpnI for the cassette and by Alw44I for the digestion of the plasmid backbone. The gel purified linear cassette is inserted on the bacterial chromosome of MG1655 carrying the Red Helper plasmid pKD46. The chromosomal section carrying the inserted fragment is transferred to HMS174(DE3) by P1 transduction. Correct insertion of the expression cassettes is confirmed by PCR (external primers (Table 3) and internal primers).

TABLE 3

Primers for Tn7 site for strains IS 5, IS 11 and IS 13

| Org. | SEQ ID NO: | Primer | Sequence |
|---|---|---|---|
| E. coli | 19 | NotI-Tn7/1-back | 5' GAT GAT GCG GCC GC G TTG CGA CGG TGG TAC G 3' |
| E. coli | 20 | EcoRI-Tn7/1-for | 5' GAT GAT GAA TTC TAT GTT TTT AAT CAA ACA TCC TG 3' |
| E. coli | 21 | XhoI-Tn7/2-back | 5' GAT GAT CTC GAG GCA TCC ATT TAT TAC TCA ACC 3' |
| E. coli | 22 | KpnI-Tn7/2-for | 5' GAT GAT GGT ACC TGA AGA AGT TCG CGC GCG 3' |
| E. coli | 23 | TN7/1 extern | 5' ACC GGC GCA GGG AAG G 3' |
| E. coli | 24 | TN7/2 extern | 5' TGG CGC TAA TTG ATG CCG 3' |

As chromosomal insertion site attTn7 is chosen (deBoy and Craig, 2000), which is situated in the non-coding region between genes gimS and phoS within the transcriptional terminator of glmS. By the specified Tn7 primers only this transcriptional terminator is replaced by the cassette. (Yu and coworkers demonstrated that homologies of 40 bp are sufficient for integration of linear fragments into the chromosome (Yu et al., 2000)). As better results are obtained with longer homologies, they are extended to 300 bp on one side and 240 bp on the other side. As HMS174(DE3) does not seem to be suitable for direct integration of linear DNA by Red Helper plasmid, MG1655 is used for initial integration and by P1 transduction the recombinant chromosomal section is transferred into HMS174(DE3). Resulting strains HMS174(DE3) T7al3GFP=IS5, HMS174(DE3)T7GFP=IS11 and HMS174 (DE3)T7112rasGFP=IS13 contain GFP under control of the T7 promoter with or without an RNA II loop structure, respectively. Correct insertion of the expression cassettes is confirmed by PCR. The obtained strains are designated I) IS5, II) IS11 and III) IS13 and tested for GFP expression and RNAI-mediated gene silencing effect in shake flask experiments.

For shake flasks experiments, overnight cultures are diluted 1:100 and grown until $OD_{600}$~0.5. Then IPTG is added for induction. Fluorescence is measured by the microplate reader SPECTRAmax GeminiXS and software, SOFTmax Pro (Molecular devices) at excitation wavelength 488 nm and emission 530 nm with a 515 nm cutoff filter.

Figure 5:
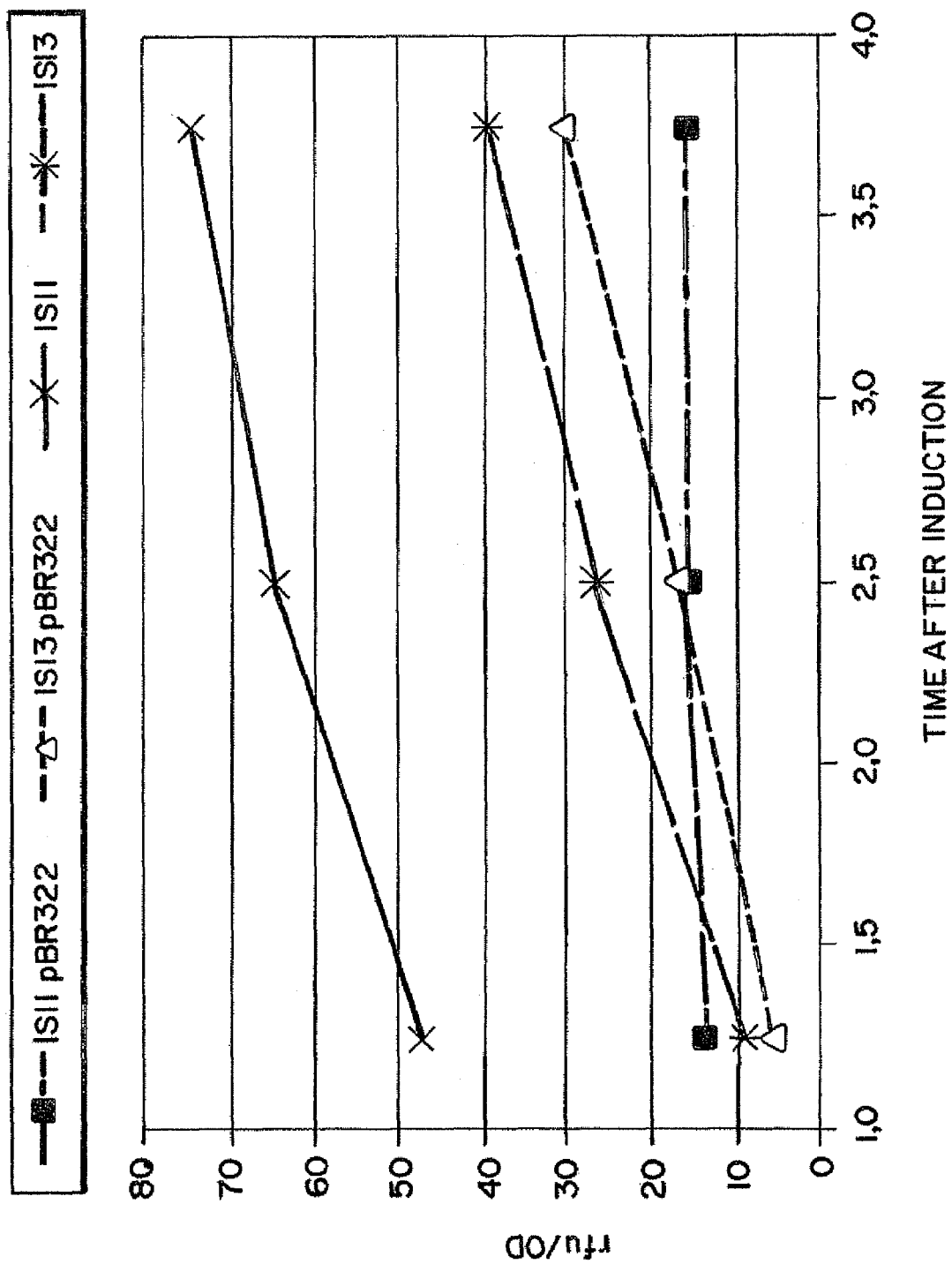
FIG. 5: Gene down-regulation effect in the presence of pBR322

Detection of GFP with and without induction with IPTG shows a clear gene silencing effect when pBR322 is present (FIG. 5). IS13 shows lower GFP expression the IS11 and inhibition of GFP expression is little, whereas IS11 shows higher GFP expression and a significant gene silencing effect providing evidence that our concept is working.

Figure 6:
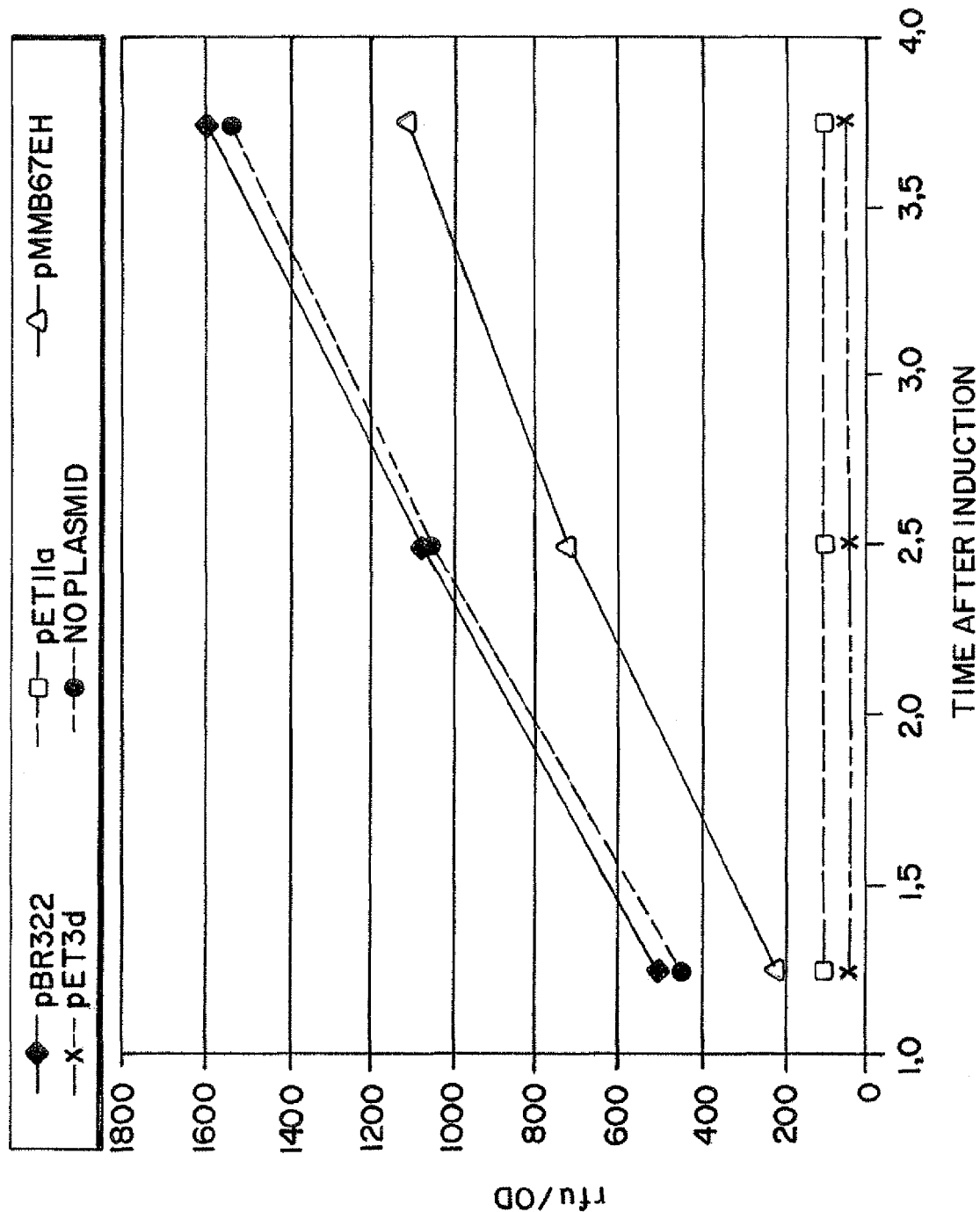
FIG. 6: Gene down-regulation effect of various plasmids

When no RNA II-like sequence is present (IS5) upstream of the GFP-gene, no gene silencing is detected (FIG. 6).

IS5 is transformed with different plasmids, including pET11a, pET3d, pMMB67EH and pBR322, to check for undesired interaction between plasmid and genomic gene expression (FIG. 6). It is found that only when the GFP mRNA contains the RNA II-like sequence and a ColE1 plasmid is used that does not contain homologous sequences to the cassette on the genome, e.g. the T7 promoter or the lac operator, a defined gene silencing effect can be observed. No interference between host and plasmid disturbs the antisense reaction when using pBR322 related plasmids that are typically used in gene therapy.

FIG. 5 shows the comparison of strains IS11 and IS13 with and without pBR322. Rfu/OD are fluorescence units related to optical density. The increase of GFP fluorescence is observed after induction in intervals of 1.5 hrs.

FIG. 6 shows the results of the shake flask experiments with IS5 containing various plasmids. pBR322 and related plasmids (as used in gene therapy applications) show no interference between host and plasmid.

EXAMPLE 3

Expression/Suppression of Marker Gene During Fermentation

The *E. coli* strains IS11 and IS5 are analyzed during a fed-batch fermentation process, with and without the presence of plasmid pBR322. Table 4 summarizes the experimental set-up of four fed-batch fermentations. Each strain is grown either in the presence or absence of pBR322.

TABLE 4

Fed batch fermentations

| Experiment | Host strain | pBR322 |
|---|---|---|
| AS1 | IS 11 | − |
| AS2 | IS 11 | + |
| AS3 | IS 5 | − |
| AS4 | IS 5 | + |

Figure 7:
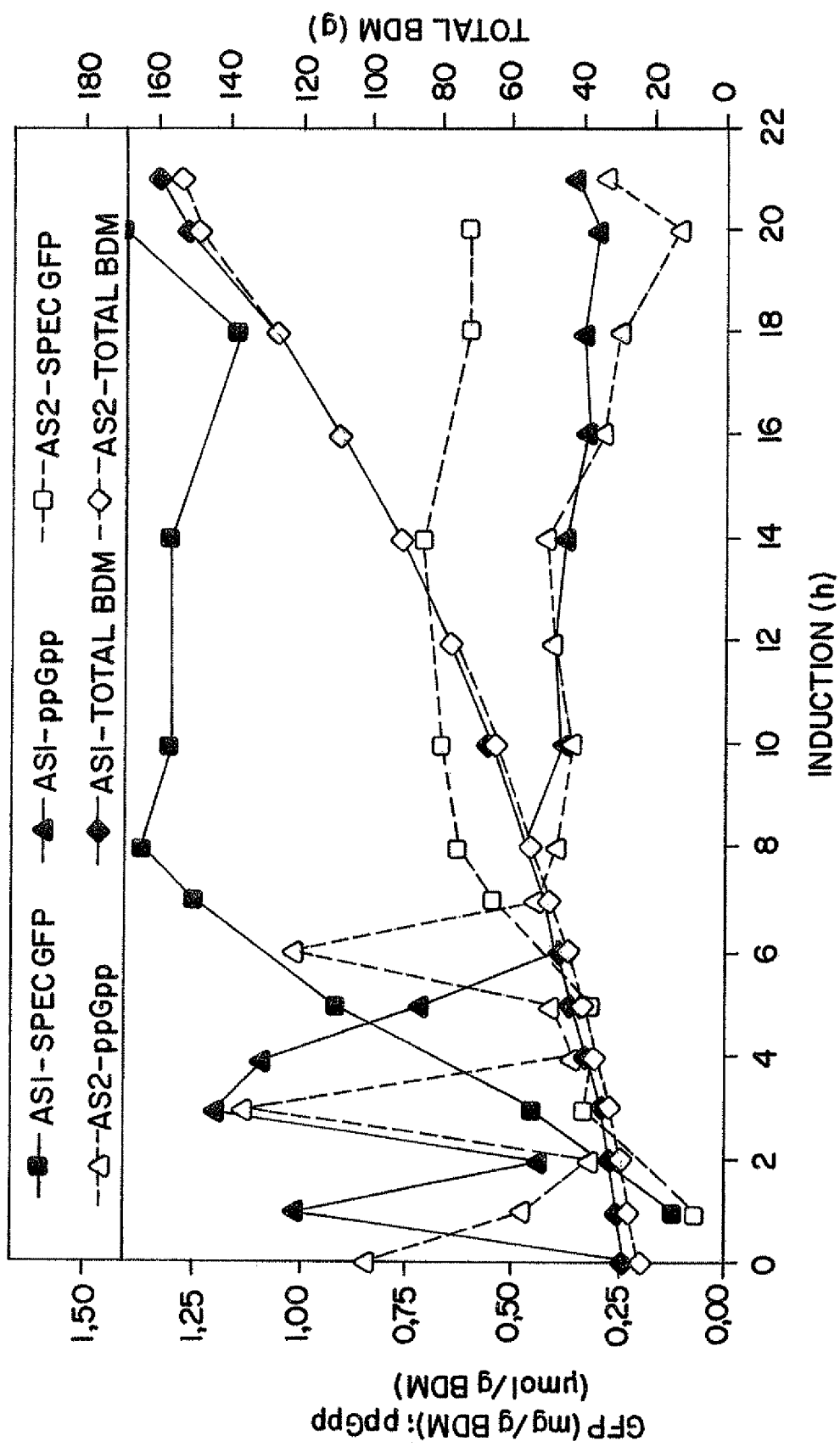
FIG. 7: Expression/suppression of marker gene during fermentation

All four cultivations show very similar trends for online signals such as $CO_2$, $O_2$, base consumption or capacity and the course of total BDM varies also in a very small range of less than ±10% from the calculated mean as shown in FIGS. 7a and 7b. FIG. 7a shows bacterial dry mass (BDM) and GFP expression of IS11 with or without maintenance of pBR322. While the total BDM is identical for both fermentations, the GFP concentration is drastically decreased when pBR322 is present (50%). The curve progression of GFP measurements strongly indicates inhibition of GFP translation by the plasmid's presence, hence, its replication, and confirms the expectation that RNA I and the modified mRNA of GFP interact, thereby hampering translation (FIG. 7a). In order to rule out that pBR322 has an effect on recombinant protein expression per se, further fed-batch experiments are carried out using IS5, again with or without plasmid propagation. As is shown in FIG. 7b, there is no difference in GFP expression or cellular growth: whether pBR322 is present in the host or not, no influence on transcription nor translation of GFP can be detected. In these experiments the overall GFP expression is much higher than when strain IS11 is used, due to efficient translation of the native mRNA. Although, protein expression is decreased by the presence of a stable RNA loop structure near the ribosomal binding site in IS11, expression is inhibited, when pBR322 is present. Thus, it can be demonstrated by using GFP as a surrogate for a toxic marker that the replication regulatory system of ColE1 can be used to suppress marker gene expression.

EXAMPLE 4

Use of a Repressor for Regulating the Expression of an Essential Gene a) Generation of Constructs for Essential Genes The first essential gene to be tested is map (Li et al., 2004), the gene for the methionine aminopeptidase, which is located at min 4 of the *E. coli* chromosome, 357 base pairs from the rpsB-tsf operon and 201 bp from the T44-RNA gene. The two genes are transcribed divergently and promoters do not overlap. This is an essential point, because the promoter of the essential gene is to be removed entirely and replaced by an inducible promoter that is specific for a chosen repressor. Chang et al, 1989 described a conditionally lethal mutant strain which has the map gene controlled by the lac promoter. By the map cassette, a 67 bp chromosomal section is replaced containing the map promoters (Chang et al, 1989). To circumvent possible transcripts from the genome, two strong transcriptional terminators T1 and T2 from the rrnB operon (Brosius et al, 1981) are added to the integration cassette.

The second gene that is tested is murA (Brown et al, 1995), which has been described as an essential *E. coli* gene. The gene murA encoding the enzyme UDP-N-acetylglucosamine enolpyruvyl transferase for the first committed step of bacterial cell wall biosynthesis, is situated on the *E. coli* chromosome at 69.3 min Herring and Blattner compared death curves of several conditional lethal amber mutants in their publication (Herring and Blattner, 2004), amongst others also those of map and murA mutants. But of all the mutations murA is far the most bactericidal showing the best and fastest killing rate in non-permissive medium.

Figure 8:
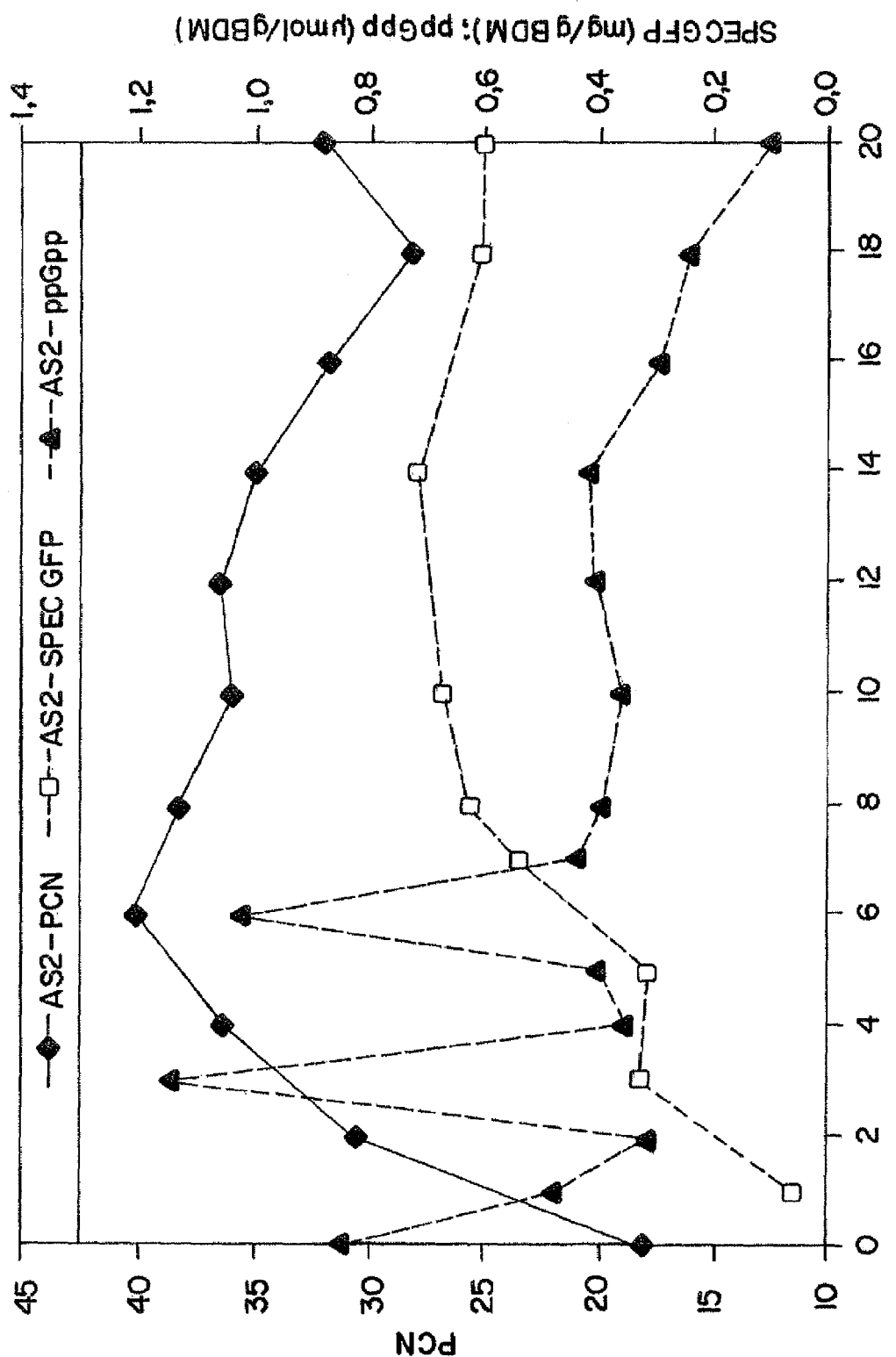
FIG. 8: Principle of a construct based on an essential gene including replacement of essential gene promoter

FIG. 8 shows the principle of a construct based on an essential gene, including replacement of essential gene promoter.

The constructs for genomic integration are cloned into vector pBluescript KSII+ again. The essential gene homologies, each ~300 bp are amplified from MG1655 colonies with primer pairs SacI-map1-for/NotI-map 1-back and XhoI-map2-back/KpnI-map2-for the map homologies and primer pairs SacI-murA 1-for/NotI-murA 1-back and XhoI-murA2-back/KpnI-murA2-for the murA homologies (for primer sequences see Table 5). The fragment containing the lactose promoter and operator (plac) is amplified from pBluescriptK-SII+ by primers BamHI-placO-back and NotI-placO-for. The gene for the chloramphenicol acetyl transferase (cat) is amplified from pLys (PACYC184) with primers HindIII-SalI-Cat-back and XhoI-Cat-for. The rrBT12 Terminators are amplified from pBAD by primers BamHI-T12-for and HindIII-T12-back. The assembled vectors pBSKmap<plac-T12-Cat> and pBSKmurA<plac-T12-Cat> are digested by SacI and KpnI and the linearized cassettes are inserted on the genome of MG1655 as described previously. Correct integration of the cassettes is verified by PCR combining external primers (map1 extern, map2 extern, murA1 extern, murA2 extern; Table 5) and internal primers.

The primers for essential and test gene constructs are shown in Table 5.

TABLE 5

| Org. | SEQ ID NO: | Primer | Sequence |
|---|---|---|---|
| E. coli | 25 | Not-map1-back | 5' ATG ATG ATG GCG GCC GCA CCG ACG CTG ATG GAC AGA ATT AAT GG 3' |
| E. coli | 26 | SacI-map1-for | 5' GCT GCT GAG CTC CCA TCT TTG ATT ACG GTG AC 3' |
| E. coli | 27 | XhoI-map2-back | 5' ATG ATG CTC GAG CGC CAA ACG TGC CAC TG 3' |
| E. coli | 28 | KpnI-map2-for | 5' GCT GCT GGT ACC GAA GTG AAC ACC AGC CTT G 3' |
| E. coli | 29 | map2 extern | 5' TTC GGG TTC CAG TAA CGG G 3' |
| E. coli | 30 | map1 extern | 5' TTT CGA GGT ATC GCC GTG G 3' |
| E. coli | 31 | SacI-murA1-for | 5' GCT GCT GAG CTC CAA AGC GCG CTA CCA GCG 3' |
| E. coli | 32 | NotI-murA1-back | 5' ATG ATG ATG GCG GCC GCT TAA CTG AGA ACA AAC TAA ATG G 3' |
| E. coli | 33 | XhoI-murA2-back | 5' ATG ATG CTC GAG GCT CAA AAG CCG TTC AGT TTG 3' |
| E. coli | 34 | KpnI-murA2-for | 5' GCT GCT GGT ACC TGC CAG CGC AAC TTT GCT C 3' |
| E. coli | 35 | murA1 extern | 5' GTA CAA CCG CCA GGT AGT G 3' |
| E. coli | 36 | murA2 extern | 5' GTC TGA TTT ATC AGC GAG GC 3' |
| E. coli | 37 | HindIII-SalI-Cat-back | 5' GCT GCT AAG CTT GTC GAC AGC CAC TGG AGC ACC TC 3' |
| E. coli | 38 | XhoI-Cat-for | 5' ATG ATG CTC GAG ACG GGG AGA GCC TGA GC 3' |
| E. coli | 39 | BamHI-T12-for | 5' ATG ATG GGA TCC AAA AGG CCA TCC GTC AGG 3' |
| E. coli | 40 | HindIII-T12-back | 5' GTC GTC AAG CTT ATA AAA CGA AAG GCT CAG TC 3' |
| E. coli | 41 | BamHI-placO-back | 5' GCT GCT GGA TCC GCG CCC AAT ACG CAA ACC 3' |
| E. coli | 42 | NotI-placO-for | 5' ATG ATG ATG GCG GCC GCT GTG AAA TTG TTA TCC GCT C 3' |

If the homology primers are chosen correctly, colonies are expected after genomic integration only in the presence of IPTG. No ribosomal binding site (RBS) is provided on the primers NotI-map/murA-for, as it is intended not to replace the native RBS by the cassette to keep gene expression pattern as normal as possible. So the aim is to replace any promoter in front of the essential gene but to keep the native RBS intact.

Figure 9:
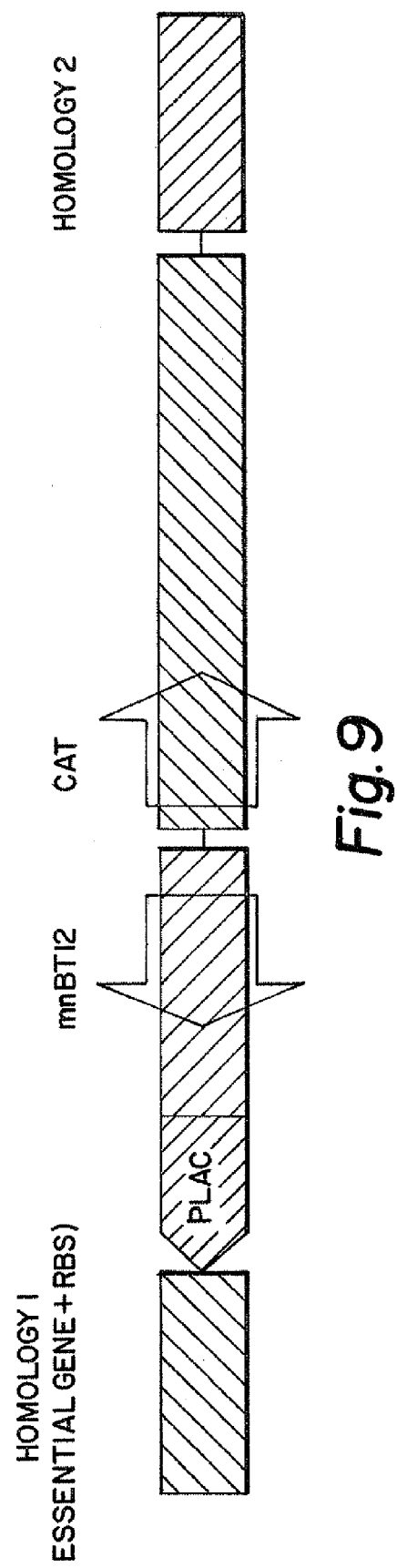
FIG. 9: Test constructs for repressing GFP as a surrogate for an essential gene

Neither the map nor the murA mutants grew on LB-CM plates after transformation, but they grew properly on LB-CM plates and liquid medium containing 0.1 mmol IPTG/L, indicating that the choice of the primers was correct and plac and the terminators are functioning properly. However, in further cultivation map mutants show slight growth on plates and liquid medium without IPTG. As murA mutants did not show any growth on non-permissive media the murA construct is chosen as a basis for the selection system.

b) Generation of Test Constructs for Repressing GFP as a Surrogate for an Essential Gene The principal of the constructs, exemplified by pBluescriptKSII+, is shown in FIG. 9. The plasmid pBSKTn7<pLtetOgfp-T7al3tetR-Cat> is constructed in several successive cloning steps from pBSKTn7<T7al3GFP> as starting vector and intermediate plasmids containing the individual fragments (for primer sequences see Table 5 and 6). The Tn7 homology 1 is amplified from a bacterial template using primers SacI-Tn7/1-back and EcoRI Tn7/1-for, Tn7 homology 2 is amplified using primers XhoI-Tn7/2-back and KpnI-Tn7/2-for, rrnBT12 terminators are amplified using primers EcoRI-T12-back and HindIII-SalI-T12 for and the cat gene is amplified by primers HindIII-SalI-Cat-back and XhoI-Cat-for. (Table 5). The tetracyclin repressor gene (tetR) is amplified from the tetracycline resistant strain IS1 (HMS174(DE3) ilv500::Tn10) containing Tn10 by primers NheI-tetR-back and BamH1H-tetR-for. The tet-inducible pLtetO promoter is fully synthesized on a primer (HindIII-PLtetO-NotI-RBS-GFP back) and together with primer EcoRI-GFP-for used to amplify gfp. For genomic integration, the assembled vector pBSKTn7<pLtetOgfp-T7al3tetR-Cat> is again digested with SacI and NotI to release the desired expression cassette.

c) Shake Flask Experiments with Test Constructs Inserted into the HMS174(DE3) (=K12) Genome HMS174(DE3)Tn7::pLtetOgfpT7aL3tetRCat (HMS-GTC) overnight cultures with and without pBR322 are diluted 1:100 in semi-synthetic medium and split up in two parallel shake flask cultures with and without the inducer IPTG. The cultures are grown by shaking at 37° C. When shake flasks reached an $OD_{600nm}$ of more than 0.7, sampling for the gfp-ELISA is started.

The shake flask experiment with HMS-GTC is performed to test if the synthetic promoter pLtetO is working and tetR with the small fusion peptide (Loop3) on its N-terminus is still efficient in operator-binding.

Figure 10:
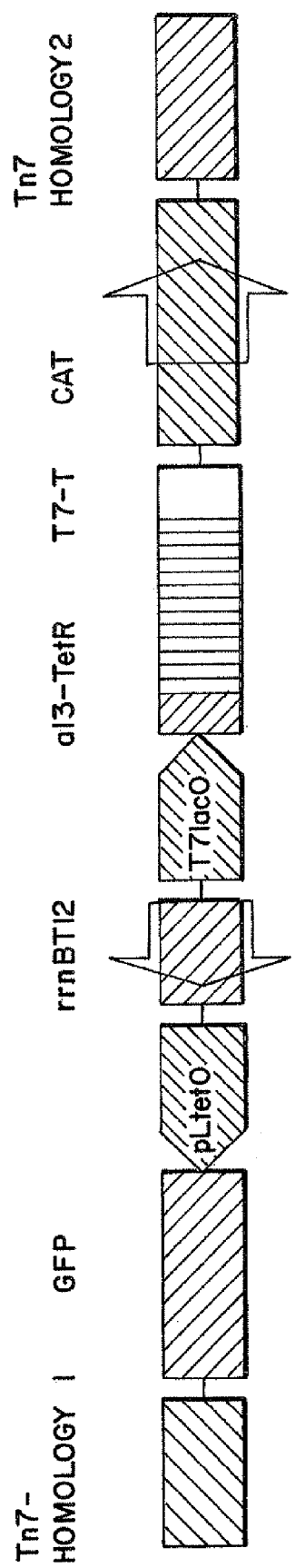
FIG. 10: Results from shake flask experiments with test constructs inserted into the HMS174(DE3) genome In Examples 1 and 2, the oligonucleotides as shown in Table 1 are used.
Figure 11:
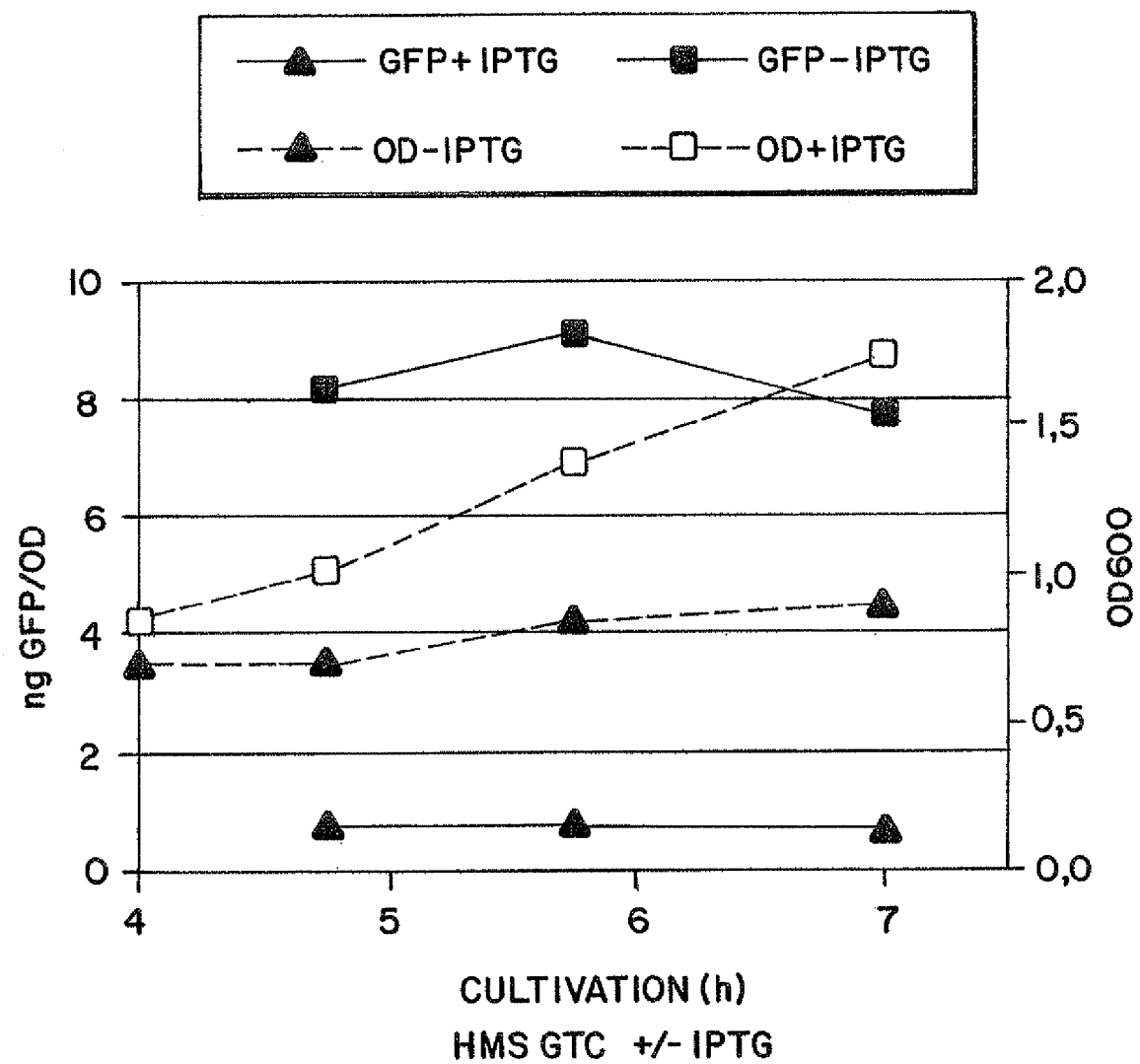

The induced media contain 0.1 mmol IPTG, and is increased to 0.5 mmol IPTG at OD 0.5. This high amount of IPTG is the reason of the growth inhibition of the induced flask (FIG. 10). IPTG addition shuts down transcription of the gftp gene, indicating that the reaction cascade functions properly. The low—and constant—basal GFP level in the induced flask is apparently caused by remaining GFP from the overnight culture without IPTG.

The HMS-GTC shake flask results are compared with shake flask experiments of the same host and MG1655-GTC containing plasmid pBR322. MG1655 lacks the DE3 prophage and thus the T7-polymerase and so serves as negative control.

Presence of pBR322 always shows increased GFP expression. In Table 7 the mean ratio (plasmid/no plasmid) of ng GFP/OD in the shake flasks is calculated and both hosts

TABLE 6

Additional Primers for test construct:

| Org. | SEQ ID NO: | Primer | Sequence |
|---|---|---|---|
| E. coli | 43 | EcoRI-T12-back | 5' GCT GCT GAA TTC ATA AAA CGA AAG GCT CAG TC 3' |
| E. coli | 44 | HindIII-SalI-T12 for | 5' GCT GCT AAG CTT GTC GAC AAA AGG CCA TCC GTC AGG 3' |
| E. coli | 45 | EcoRI-Tn7/1-for | 5' GAT GAT GAA TTC TAT GTT TTT AAT CAA ACA TCC TG 3' |
| E. coli | 46 | SacI-Tn7/1-back: | 5' GAT GAT GAG CTC GTT GCG ACG GTG GTA CG 3' |
| E. coli | 47 | XhoI-Tn7/2-back | 5' GAT GAT CTC GAG GCA TCC ATT TAT TAC TCA ACC 3' |
| E. coli | 48 | KpnI-Tn7/2-for | 5' GAT GAT GGT ACC TGA AGA AGT TCG CGC GCG 3' |
| E. coli | 49 | NheI-tetR-back | 5' GCT GCT GCT AGC ATG ATG TCT AGA TTA GAT AAA AG 3' |
| E. coli | 50 | BamHI-tetR-for | 5' GCT GCT GGA TCC TTA AGA CCC ACT TTC ACA TTT AAG 3' |
| A. victoria | 51 | EcoRI GFP for | 5' GTC GTC GAA TTC TTA TTT GTA TAG TTC ATC CAT GC 3' |
| (A. victoria, E. coli, Lambda) | 52 | HindIII-PLtetO-NotI-RBS-GFP back | 5' GCT GCT AAG CTT TCC CTA TCA GTG ATA GAG ATT GAC ATC CCT ATC AGT GAT AGA GAT ACT GAG CAC ATC GCG GCC GCT TTA AGA AGG AGA TAT ACA TAT GCG TAA AGG AGA AGA AC 3' | containing a chromosomal copy of the cassette as well as different induction strategies are compared.

TABLE 7

| Host | Induction | Mean Ratio [ng GFP/OD] (+plasmid/−plasmid) | Conclusion |
|---|---|---|---|
| MG1655-GTC | no induction | 1.43 | — |
| HMS-GTC | ind. at start of cultivation | 1.44 | no effect |
|  | ind. at OD = 0.5 | 2.69 | plasmid effect |
|  | no induction | 2.29 | plasmid effect |

When HMS-GTC containing the plasmid is induced at the start of cultivation, a slight increase (factor 1.44) in GFP expression is measured compared to the flask without plasmid. However, this slight increase (factor 1.43) is also measured in MG1655-GTC indicating that this GFP cumulation is probably caused by the plasmid but not by RNAI-antisense reaction.

Completely different results are obtained when IPTG is added when an $OD_{600nm}$ of 0.5 is reached. Although basal GFP level is higher, there is a definite raise in GFP expression, when pBR322 is present in the cell. Here RNAI and its antisense reaction with the loop3 of RNAII is the antagonist of the inducer IPTG. However, IPTG is a strong inducer and RNAI-loop3 antisense reaction is comparatively weak.

Also a more than double increase (factor 2.29) of GFP is observed in HMS-GTC pBR322 without induction (Table 7). This can be explained by the leakiness of T7 system (Studier and Mofatt, 1986) and is also an indirect proof of the antisense reaction. Due to the basal level of T7-polymerase, small amounts of TetR are present in the cell. And since TetR is a strong and efficient repressor molecule, this small amount is sufficient to suppress GFP expression to a factor of 2.29. When RNAI from pBR322 is present, it is able to "handle" the few tetR mRNA molecules and GFP level raises.

REFERENCES

Balbas, P., Soberon, X., Bolivar, F. and Rodriguez, R. L.: The plasmid, pBR322. Biotechnol 10, 5-41 (1988)
Balbas, P., (2001). Understanding the Art of Producing Protein and Nonprotein Molecules in *Escherichia coli*. Mol. Biotechnol. November; 19(3):251-67.
Bahl., C. P., Wu, R., Stawinsky, J., Narang, S. A. (1977) Minimal length of the lactose operator sequence for the specific recognition by the lactose repressor. Proc. Natl. Acad. Sci. USA 74, 966-970.
Beck, C. F., Mutzel, R. Barbé, J., Müller, W. A. (1982) A multifunctional gene (tetR) controls Tn10-encoded tetracycline resistance. J. Bacteriol. 150, 633-642.
Bernard, P., Couturier, M. (1992). Cell killing by the F plasmid CcdB protein involves poisoning of DNA topoisomerase II complexes. J Mol. Biol., August 5, 226:3 735-45
Bhagwat, A. S, and Person, S.: Structure and properties of the region of homology between plasmids pMB1 and ColE1. Mol Gen Genet. 182, 505-507 (1981)
Bolivar, F.: Molecular cloning vectors derived from the CoLE1 type plasmid pMB1. Life Sci 25, 807-817 (1979)
Brosius J, Ullrich A, Raker M A, Gray A, Dull T J, Gutell R R, Noller H F (1981): Construction and fine mapping of recombinant plasmids containing the rrnB ribosomal RNA operon of *E. coli*. Plasmid. July; 6(1):112-8.
Brown, E. D., Vivas, E. I., Walsh C. T., Kolter, R. (1995): MurA (MurZ), the enzyme that catalyzes the first committed step in peptidoglycan biosynthesis, is essential in *Escherichia coli*. Journal of Bacteriology, Vol. 177, No. 14, 4194-4197.
Casali, N., (2003), *Escherichia coli* host strains. Methods Mol. Biol. 253, 27-48.
Cesare ni, G., Helmer-Citterich, M., Castagnoli, L. (1991). Control of ColE1 plasmid replication by antisense RNA. Trends Genet. July 7:7, 230-5
Chan, P. T., Ohmori, H., Tomizawa, J., Lebowitz, J. (1985). Nucleotide sequence and gene organization of ColE1 DNA. J Biol Chem, 1985, Jul. 25, 260:15, 8925-35
Chang, A. C. Y., and Cohen, S. N. Construction and characterization of amplifiable multicopy DNA cloning vehicles derived from the P15A cryptic miniplasmid. Journal J. Bacteriol. Vol. 134, 1141 1156, (1978)
Chang S Y, McGary E C, Chang S. (1989). Methionine aminopeptidase gene of *Escherichia coli* is essential for cell growth. J. Bacteriol. July; 171(7):4071-2
Chen, W., Graham, C., and Ciccare lli, R. B. (1997). Automated fed-batch fermentation with feed-back controls based on dissolved oxygen (DO) and pH for production of DNA vaccines. J. Ind. Microbiol. Biotechnol., 18, 43-48.
Craig, N. L: Transposon TN7. In Berg, D. E and Howe, M. H. (Eds.), Mobile DNA. American Society of Microbiology, Washington D.C., (1989), 211-225.
Crozat, A., Aman, P., Mandahl, N., Ron, D. (1993). Fusion of CHOP to a novel RNA binding protein in human myoxid liposarcoma. Nature 363, 640-644
Datsenko, K., and Wanner, B. (2000). One-step inactivation of chromosomal genes in *Escherichia coli* K-12 using PCR products. PNAS. June 6, Vol. 97, No. 12, 6640-6645.
Davison, J. (2002). Towards safer vectors for the field release of recombinant bacteria. Environ. Biosafety Res. 1:9-18.
DeBoy R T and Craig N L. (2000), Target site selection by Tn7: attTn7 transcription and target activity. J. Bacteriol. 2000 June; 182(11):3310-3.
Diaz, R. and Staudenbauer, W. L.: Origin and direction of mini-R1 plasmid DNA replication in cell extracts of *Escherichia coli*. J. Bacteriol. (1982) June; 150(3): 1077-1084
Eguchi, Y., Itoh, T., Tomizawa, J. (1991a). Antisense RNA. Annu Rev Biochem 60:631-52.
Eguchi, Y., and Tomizawa, J. (1991b). Complexes formed by complementary RNA stem loops: Their formations, structures and interaction with ColE1Rom protein. J Mol Biol 220:831-842.
Fürste, J., Pansegrau, W., Frank, R., Blocker, H., Scholz, P., Bagdasarian, M., Lanka, E. (1986). Molecular cloning of the plasmid RP4 primase region in a multi-host-range tacP expression vector. Gene, 48:119-131.
Gay, P., Le Coq, D., Steinmetz, M., Ferrari, E., Hoch, J. A. (1983). Cloning structural gene sacB, which codes for exoenzyme levansucrase of *Bacillus subtilis*: expression of the gene in *Escherichia coli*. J. Bacteriol., March; 153(3): 1424-31.
Gerdes S. Y., Scholle M. D., D'Souza M., Bemal A., Baev M. V., Farrell M., Kumasov O. V., Daugherty M. D., Mseeh F., Polanuyer B. M., Campbell J. W., Anantha S., Shatalin K. Y., Chowdhury S. A. K., Fonstein M. Y., Osterman A. L. (2002). From genetic footprinting to antimicrobial drug targets: Examples in cofactor biosynthetic pathways. Journal of Bacteriology, August 2002, Vol. 184, No. 16, pp 4555-4572.
Gerdes S Y, Scholle M D, Campbell J W, Balazsi G, Ravasz E, Daugherty M D, Somera A L, Kyrpides N C, Anderson I, Gelfand M S, Bhattacharya A, Kapatral V, D'Souza M, Baev M V, Grechkin Y, Mseeh F, Fonstein M Y, Overbeek R, Barabasi A L, Oltvai Z N, Osterman A L. (2003) Experimental determination and system level analysis of essential genes in *Escherichia coli* MG1655. J. Bacteriol. 185, 5673-84.

Gilbert, W. and Maxam, A. (1973) Proc. Natl. Acad. Sci. USA 70, 3581-3584.

Gregorian, R., and Crothers, D. (1995). Determinants of RNA Hairpin Loop-Loop Complex Stability. J Mol Biol 248: 968-984.

Guzman, L. M., Belin, D., Carson, M., Beckwith, J. (1995). Tight regulation, modulation, and high-level expression by vectors containing the arabinose pBAD Promoter. Journal of Bacteriology. Vol. 177, 14: 4121-4130.

Hägg, P., Wa de Pohl, J., Abdulkarim, F., Isaksson, L. (2004) A host/plasmid system that is not dependent on antibiotic resistance genes for stable plasmid maintenance in *Escherichia coli*. J. Biotechnology 111, 17-30.

Haidinger, W., Szostak, M. P., Jechlinger, W., Lubitz, W. Online monitoring of *Escherichia coli* ghost production. Appl. Environ. Microbiol. January 2002, 468-474.

Helinski, Toukdarian, A. and Novick, R.: Replication control and other stable maintenance mechanisms of plasmids. In: *Escherichia coli* and *Salmonella*. Cellular and Molecular Biology. Ed: Neidhardt F., American Society for Microbiology Press, Washington, D.C., 2295-2324 (1996)

Herring, C. D., Blattner, F. R. (2004). Conditional lethal amber mutations in essential *Escherichia coli* genes. Journal of Bacteriology, Vol. 186, No. 9, 2673-2681.

Jacob, F., Monod, J. (1961) Genetic regulatory mechanism in the synthesis of proteins. Journal of Molecular Biology 3, 318-356.

Jensen, L. B., Ramos, J. L., Kaneva, Z., Molin, S. (1993). A substrate-dependent biological containment system for *Pseudomonas putida* based on the *Escherichia coli* gef gene. Appl Environ Microbiol., November 59:11, 3713-7

Jonasson, P., et al., (2002). Genetic design for facilitated production and recovery of recombinant proteins in *Escherichia coli*. Biotechnol. Appl. Biochem. 35, 91-105

Kaplan, D. L., Mello, C., Sano, T., Cantor, C., Smith, C. (1999). Streptavidin-based containment systems for genetically engineered microorganisms. Biomol Eng 1999, December 31 16:1-4 135-40.

Klemm, P., Jensen, L. B., Molin, S. (1995). A stochastic killing system for biological containment of *Escherichia coli*. Appl Environ Microbiol. February 61:2, 481-6.

Knudsen, S., Saadbye, P., Hansen, L. H., Collier, A., Jacobsen, B. L., Schlundt, J., Karlstrom, O. H. (1995). Development and testing of improved suicide functions for biological containment of bacteria. Appl Environ Microbiol., March 61:3 985-91.

Kues, U. and Stahl, U. (1989): Replication of plasmids in gram negative bacteria. Microbiol. Rev 53, 491-516

Lahijani, R., Hulley, G., Soriano, G., Horn, N. A., and Marquet, M. (1996). High-yield production of pBR322-derived plasmids intended for human gene therapy by employing a temperature-controllable point mutation. Hum. Gene Ther. 7, 1971-1980.

Li J Y, Chen L L, Cui Y M, Luo Q L, Gu M, Nan F J, Ye Q Z. Characterization of full length and truncated type I human methionine aminopeptidases expressed from *Escherichia coli*. (2004) Biochemistry 43, 7892-8.

Lin, E. C. C., Bacteria, Plasmids, and Phages: An Introduction to Molecular Biology. (1984). Cambridge, Mass.: Harvard University Press, 1'-18.

Lin-Chao, S., and Cohen, S. N. (1991). The rate of processing and degradation of antisense RNA I regulates the replication of ColE1-type plasmids in vivo. Cell. June 28, 65:7 1233-42.

Malmgren, C., Engdahl, H., Romby, B., Wagner, G. (1996). An antisense/target RNA duplex or a strong intramolecular RNA structure 5' of a translation initiation signal blocks ribosome binding: The case of plasmid R1. RNA 1: 1022-1032.

Merlin, S., and Polisky, B. (1995). Assessment of quantitative models for plasmid ColE1 copy number control. J Mol. Biol., April 28, 248:2, 211-9

O'Kennedy, R. D., Baldwin, C., and Keshavarz-Moore, E., (2000). Effects of growth medium selection on plasmid DNA production and initial processing steps. J. Biotechnol. 76, 175-183.

O'Kennedy et al., (2003). Effects of fermentation strategy on the characteristics of plasmid DNA production. Biotechnol Appl. Biochem. 34, 83-90.

Postle, K., Nguyen, T. T., Bertrand, K. P. (1984) Nucleotide sequence of the repressor gene of the TN10 tetracycline resistance determinant. Nucleic Acids Res. 12, 4849-4863.

Rawlings, D. E. (1999) Proteic toxin-antitoxin, bacterial plasmid addiction systems and their evolution with special reference to the pas system of pTF-FC2. FEMS Microbiology Letters, 176, 269 277.

Reinikainen, P., Korpela, K., Nissinen, V., Olkku, J., Soderlund, H., and Markkanen, P. (1988). *Escherichia coli* plasmid production in Fermenter. Biotech. Bioeng. 33, 386-393.

Ringquist, S., MacDonald, M., Gibson, T., Gold, L. (1993). Nature of the ribosomal mRNA track: Analysis of ribosome-binding sites containing different sequences and secondary structures. Biochemistry. 32:10254-10262.

Rogers, M., Ekaterinaki, N., Nimmo, E., Sherratt, D., Analysis of Tn7 transposition. Mol Gen Genet (1986), December 205:3 550-6

Ronchel, M. C., Molina, L., Witte, A., Lubitz, W., Molin, S., Ràmos, J. I., Ramos, C. (1998), Characterization of cell lysis in *Peudomonas putida* induced upon expression of heterologous killing genes. Appl. Environ. Microbiol. 64: 4904-4911.

Rouch, D. A., Brown N. L. (1997) Copper-inducible transcriptional regulation at two promoters in the *Escherichia coli* copper resistance determinant pco. Microbiology 143, 1191-1202.

Sano, T., Pandori, M., Chen, X., Smith, C., Cantor, C. (1995). Recombinant core streptavidins. The Journal of Biological Chemistry. Vol. 270, 47: 28204-28209.

Studier, F. W., Moffatt, B. A. (1986). Use of bacteriophage T7 RNA polymerase to direct selective high-level expression of cloned genes. J Mol. Biol., May 5, 189:1 113-30.

Szafranski, P., Mello, C. M., Sano, T., Smith, C. L., Kaplan, D. L., Cantor, C. R. (1997). A new approach for containment of microorganisms: dual control of streptavidin expression by antisense RNA and the T7 transcription system. Proc Natl Acad Sci USA. February 18, 94:4 1059-63.

Tomizawa, J. and Itoh, T. (1981). Plasmid ColE1 incompatibility determined by interaction of RNA I with primer transcript. Proc Natl Acad Sci USA 78, 6096-6100

Tomizawa, J. (1984). Control of ColE1 plasmid replication: the process of binding of RNA I to the primer transcript. Cell 38, 861-870

Tomizawa, J. (1986). Control of Plasmid Replication: Binding of RNA I to RNA II and Inhibition of Primer Formation. Cell. 47:89-97.

Tomizawa, J. (1989). Control of ColE1 Plasmid Replication: Intermediates in the binding of RNA I and RNA II. J Mol Biol 212:683-694.

Tomizawa J. (1990). Control of ColE1 plasmid replication. Interaction of Rom protein with an unstable complex formed by RNA I and RNA II. J Mol. Biol. April 20; 212(4):695-708

Torres, B., Jaenecke, S., Timmis, K. N., Garcia, J. L., Diaz, E. (2000). A gene containment strategy based on a restriction-modification system. Environ Microbiol., October 2:5, 555-63.

Tsien, R. Y. (1998). The green fluorescent protein. Annu Rev Biochem., 67:509-44

Vieira, J. and Messing, J.: The pUC plasmids, an M13 mp 7-derived system for insertion mutagenesis and sequencing with synthetic universal primers. Gene 19, 259-268 (1982)

Waddell, C. S., and Craig, N. L. (1988), Tn7 transposition: two transposition pathways directed by five Tn7-encoded genes. Genes Dev, February 2:2, 137-49

Wang, et al. (2001). Medium design for Plasmid DNA based on stoichimetric model. Proc. Biochem. 36, 1085-1093.

Wiliams, S., Cranenburgh, R., Weiss, A. Repressor titration: a novel system for selection and stable maintenance of recombinant plasmids. Nucleids Acids Research, (1998), Vol 26, No. 9; 2120-2124

Yanofski, C., Crawford, I. P. (1987) The tryptophan operon. In Neidhardt, F. C., Ingraham, J. L., Low, K. B., Magasanik, B., Schaechter, M., Umbarger, H. E., editors: Neidhardt, F. C., Ingraham, J. L., Low, K. B., Magasanik, B., Schaechter, M., Umbarger, H. E. Escherichia coli and Salmonella typhimurium: cellular and bolecular biology. Washington D.C., American Society for Microbiology, pp 1453-1472.

Yu, D., Ellis, H., Lee, C., Jenkins, N., Copeland, N., Court, D. (2000). An efficient recombination system for chromosome engineering in Escherichia coli. PNAS. May 23, Vol. 987, No. 11, 5978-5983.

Zhang, Y., Nelson, M., Nietfeldt, J., Burbank, D. E., Van Etten, J. L. (1992). Characterization of Chlorella virus PBCV-1 CviAII restriction and modification system. Nucleic Acids Research, Vol. 20, 20: 5351 5356.

Zuker, M., Mathews, D., Turner, D. (1999), Algorithms and Thermodynamics for RNA Secondary Structure Prediction: A Practical Guide. In RNA Biochemistry and Biotechnology, J. Barciszewski & B. F. C. Clark, eds., NATO ASI Series, Kluwer Academic Publishers.

The invention claimed is:

1. A non-naturally occurring bacterial cell containing
   i) a DNA sequence encoding a marker protein, the expression of which is to be regulated, operably associated to
   ii) a DNA sequence encoding a part of an RNA II sequence
      a) that is complementary to an RNA I sequence from a plasmid with a ColE1 origin of replication, and
      b) that is positioned upstream or downstream of the ribosomal binding site of the DNA sequence of i), such that in the absence of RNA I in said bacterial cell the mRNA of the DNA sequence of i) is translated into a marker protein,
   wherein said part is a two loop structure of the RNA II sequence,
   wherein said bacterial cell contains said DNA sequences i) and ii) integrated in its genome.

2. The bacterial cell of claim 1, wherein said DNA sequence i) is a DNA sequence that is foreign to said cell.

3. The bacterial cell of claim 2, wherein said foreign DNA sequence i) encodes a marker protein that is lethal or toxic to said cell.

4. The bacterial cell of claim 3, wherein said foreign DNA sequence i) is under the control of an inducible promoter.

5. The bacterial cell of claim 3, wherein said foreign DNA sequence i) encodes a marker protein that is lethal or toxic to said cell per se or by generating a toxic substance.

6. The bacterial cell of claim 3, wherein said foreign DNA sequence i) encodes a repressor protein that is lethal or toxic to said bacterial cell by repressing the transcription of a gene that is essential for growth of said cell.

7. The bacterial cell of claim 6, wherein said essential gene is operably linked to a promoter which contains a DNA sequence that is specifically bound by said repressor protein.

8. The bacterial cell of claim 7, wherein said promoter linked to said essential gene is inducible.

9. The bacterial cell of claim 8, wherein said inducible promoter is inducible independent of the inducible promoter controlling foreign DNA sequence i).

10. The bacterial cell of claim 1, wherein said DNA sequence ii) is inserted between the ribosomal binding site and the start codon of said DNA sequence i).

11. The bacterial cell of claim 1, wherein said DNA sequence i) and said DNA sequence ii) are linked such that they encode a fusion protein.

12. The bacterial cell of claim 1, wherein said DNA sequence i) and said DNA sequence ii) are translationally coupled.

13. The bacterial cell of claim 1 that has the ability to replicate a plasmid with a ColE1 origin of replication.

14. The bacterial cell of claim 13, wherein said cell is an *Escherichia coli* cell.

15. A host-vector system comprising
   a) a plasmid with a ColE1 origin of replication capable of transcribing RNA I;
   b) a bacterial host cell in which said plasmid a) can be replicated, containing
      i) a DNA sequence encoding a marker protein, the expression of which is to be regulated, operably associated to
      ii) a DNA sequence encoding a part of an RNA II sequence that is complementary to an RNA I sequence from the plasmid a) and that is positioned upstream or downstream of the ribosomal binding site of the DNA sequence of i), such that in the absence of RNA I in said bacterial cell the mRNA of the DNA sequence of i) is translated into a marker protein,
      wherein said part is a two loop structure of the RNA II sequence,
      wherein in the presence of RNA I in said bacterial cell the translation of the marker protein is completely or partially suppressed,
      wherein said bacterial host cell contains DNA sequences i) and ii) integrated into its genome.

16. The host-vector system of claim 15, wherein said DNA sequence i) encodes a marker protein that is lethal or toxic to said bacterial cell and wherein said RNA sequence defined in ii), in the absence of the plasmid a), allows for expression of said lethal or toxic protein such that growth of said host cell is completely or partially inhibited and wherein, when said plasmid a) is present inside said host cell, the RNA I molecule transcribed from the plasmid hybridizes with said RNA sequence defined in ii), whereby expression of said lethal or toxic protein is suppressed such that said complete or partial growth inhibition is abrogated in plasmid-bearing cells.

17. The host-vector system of claim 15, wherein said plasmid a) additionally contains a gene of interest.

18. A method for producing plasmid DNA, comprising the steps of
   i) transforming a population of bacterial host cells of claim 3 with a plasmid that has a ColE1 origin of replication and contains a gene of interest that is not to be expressed from said plasmid in said bacterial host cell,
   ii) growing said bacterial host cell population under conditions in which said lethal or toxic protein is expressible in the cells, whereby expression of said protein completely or partially inhibits growth of plasmid-free cells such that the plasmid-bearing cells outgrow the plasmid-free cells,
   iii) harvesting plasmid-bearing cells, and
   iv) isolating and purifying the plasmid DNA.

19. A method for producing a protein of interest, comprising the steps of
   i) transforming a population of bacterial host cells of claim 3 with a plasmid that has a ColE1 origin of replication and contains a DNA sequence encoding a protein of interest under the control of a prokaryotic promoter that enables expression of said protein in said bacterial host cells,
   ii) growing said bacterial host cell population under conditions in which said lethal or toxic protein is expressible in the cells, whereby expression of said protein completely or partially inhibits growth of plasmid-free cells such that the plasmid-bearing cells outgrow the plasmid-free cells,
   iii) harvesting the protein of interest, and
   iv) isolating and purifying it.

20. The bacterial cell of claim 2, wherein said foreign DNA sequence i) encodes a repressor protein that represses the transcription of a gene that is essential for growth of said cell.

21. The bacterial cell of claim 13, further comprising a plasmid with a ColE1 origin of replication capable of transcribing RNA I, wherein the translation of the marker protein is completely or partially suppressed in the presence of RNA I in said bacterial cell.

22. The bacterial cell of claim 1, wherein said DNA sequence ii) is positioned upstream or downstream of the ribosomal binding site of the DNA sequence of i), upstream of a start codon of said marker gene and downstream of a promoter.

23. The bacterial cell of claim 22, wherein said marker protein is a marker protein that is lethal or toxic to said cell.

24. The host-vector system of claim 15, wherein said DNA sequence ii) is positioned upstream or downstream of the ribosomal binding site of the DNA sequence of i), upstream of a start codon of said marker gene and downstream of a promoter.

25. The host-vector system of claim 16, wherein said DNA sequence ii) is positioned upstream or downstream of the ribosomal binding site of the DNA sequence of i), upstream of a start codon of said marker gene and downstream of a promoter.

* * * * *